(12) United States Patent
Chen et al.

(10) Patent No.: US 9,498,448 B2
(45) Date of Patent: *Nov. 22, 2016

(54) PHARMACEUTICAL COMPOSITIONS COMPRISING MONOTERPENES

(71) Applicant: NEONC Technologies, Inc., Los Angeles, CA (US)

(72) Inventors: Thomas Chen, La Canada, CA (US); Daniel Levin, La Canada, CA (US); Satish Puppali, Rancho Cucamonga, CA (US)

(73) Assignee: NeOne Technologies, Inc., Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/843,097

(22) Filed: Sep. 2, 2015

(65) Prior Publication Data

US 2016/0039730 A1    Feb. 11, 2016

Related U.S. Application Data

(63) Continuation of application No. 13/939,834, filed on Jul. 11, 2013, now Pat. No. 9,133,085, which is a continuation of application No. 13/040,059, filed on Mar. 3, 2011, now Pat. No. 8,507,734.

(60) Provisional application No. 61/310,231, filed on Mar. 3, 2010.

(51) Int. Cl.
| | |
|---|---|
| C07C 35/18 | (2006.01) |
| A61K 31/045 | (2006.01) |
| C07C 29/92 | (2006.01) |
| C07C 67/14 | (2006.01) |
| C07C 201/12 | (2006.01) |
| C07C 29/78 | (2006.01) |
| C07C 29/88 | (2006.01) |
| C07C 201/16 | (2006.01) |
| A61K 31/4188 | (2006.01) |
| A61K 45/06 | (2006.01) |
| A61N 5/10 | (2006.01) |

(52) U.S. Cl.
CPC ......... *A61K 31/045* (2013.01); *A61K 31/4188* (2013.01); *A61K 45/06* (2013.01); *A61N 5/10* (2013.01); *C07C 29/78* (2013.01); *C07C 29/88* (2013.01); *C07C 29/92* (2013.01); *C07C 67/14* (2013.01); *C07C 201/12* (2013.01); *C07C 201/16* (2013.01); *C07B 2200/07* (2013.01); *C07C 2101/16* (2013.01)

(58) Field of Classification Search
USPC ........................................ 568/437, 854, 875
See application file for complete search history.

(56) References Cited

U.S. PATENT DOCUMENTS 7,056,491 B2    6/2006    Gould et al.

OTHER PUBLICATIONS

Kasai; Bioorganic and Medicinal Chemistry, 1993, vol. 1, No. 1, 67-70.*
Chinese Search report issued in corresponding Chinese Application No. 2015100698889 on Dec. 28, 2015.

* cited by examiner

*Primary Examiner* — Pancham Bakshi
(74) *Attorney, Agent, or Firm* — Leason Ellis LLP

(57) ABSTRACT

The present invention provides a process for purifying a monoterpene or sesquiterpene having a purity greater than about 98.5% (w/w). The process comprises the steps of derivatizing the monoterpene (or sesquiterpene) to produce a monoterpene (or sesquiterpene) derivative, separating the monoterpene (or sesquiterpene) derivative, and releasing the monoterpene (or sesquiterpene) from the derivative. Also encompassed by the scope of the present invention is a pharmaceutical composition comprising a monoterpene (or sesquiterpene) having a purity greater than about 98.5% (w/w). The purified monoterpene can be used to treat a disease such as cancer. The present monoterpene (or sesquiterpene) may be administered alone, or may be co-administered with radiation or other therapeutic agents, such as chemotherapeutic agents.

9 Claims, 22 Drawing Sheets

Combination effect of POH with DMC in various glioma cell lines

➤ Control: Negative (medium only) and Basic (cultured cells only)
➤ TEER at 0.01% (triplicate)
➤ TEER at 0.02% (triplicate)
➤ TEER at 0.03% (triplicate)

C: Control (no treatment)
S: Sigma POH 1.5 mM
G: Purified POH 1.5 mM

C: Control (no treatment)
S: Sigma POH
G: Purified POH

PHARMACEUTICAL COMPOSITIONS COMPRISING MONOTERPENES

CROSS REFERENCE TO RELATED APPLICATIONS

This application is a continuation of U.S. application Ser. No. 13/939,834 filed Jul. 11, 2013, now U.S. Pat. No. 9,133,085, issued Sep. 15, 2015, which is a continuation of U.S. application Ser. No. 13/040,059 filed Mar. 3, 2011, now U.S. Pat. No. 8,507,734, issued Aug. 13, 2013 which claims priority to U.S. Provisional Application No. 61/310,231 filed Mar. 3, 2010, the disclosures of which are incorporated by reference in their entirety.

FIELD OF THE INVENTION

The present invention relates to monoterpene or sesquiterpene compositions. In particular, the present invention relates to using monoterpenes (such as (S)-perillyl alcohol) or sesquiterpenes having a purity greater than about 98.5% (w/w) to treat nervous system tumors.

BACKGROUND OF THE INVENTION

Malignant gliomas, the most common form of central nervous system (CNS) cancers, are currently considered essentially incurable. Among the various malignant gliomas, anaplastic astrocytomas (Grade III) and glioblastonia multiforme (GBM; Grade IV) have an especially poor prognosis due to their aggressive growth and resistance to currently available therapies. The present standard of care for malignant gliomas consists of surgery, ionizing radiation, and chemotherapy. Despite recent advances in medicine, the past 50 years have not seen any significant improvement in prognosis for malignant gliomas. Wen et al. Malignant gliomas in adults. *New England J Med.* 359: 492-507, 2008. Stupp et al. Radiotherapy plus concomitant and adjuvant temozolomide for glioblastoma. *New England J Med.* 352: 987-996, 2005.

A major reason for the poor prognosis of malignant gliomas is the difficulty in delivering a sufficient quantity of chemotherapeutic agents to the brain. Drug access to the brain is limited by the blood brain barrier (BBB). The concentration of drugs that finally reach the brain is further decreased by hepatic first-pass metabolism and urinary excretion. Therefore, invasive surgeries are often required, such as tumor resection, stereotactic injection of anti-tumor medication, or placement of catheters for convection enhanced delivery of medication.

Intranasal delivery of a drug offers a novel non-invasive therapy to bypass the blood brain barrier and to rapidly deliver pharmaceutical agents to the CNS directly. Intranasally administered drugs reach the parenchymal tissues of the brain, spinal cord and/or cerebrospinal fluid (CSF) within minutes. In addition to delivery via the olfactory tract and trigeminal nerves, it appears from animal studies that the therapeutic drug is also delivered systemically through the nasal vasculature. Hashizume et al. New therapeutic approach for brain tumors: intranasal delivery of telomerase inhibitor GRN163. *Neuro-oncology* 10: 112-120, 2008. Thorne et al. Delivery of insulin-like growth factor-1 to the rat brain and spinal cord along olfactory and trigeminal pathways following intranasal administration. *Neuroscience* 127: 481-496, 2004. Intranasal delivery of therapeutic agents may provide a systemic method for treating other types of cancers, such as lung cancer, prostate cancer, breast cancer, hematopoietic cancer and ovarian cancer, etc.

Perillyl alcohol (POH), a naturally occurring monoterpene, has been suggested to be an effective agent against a variety of cancers, including CNS cancer, breast cancer, pancreatic cancer, lung cancer, melanomas and colon cancer. Gould, M. Cancer chemoprevention and therapy by monoterpenes. *Environ Health Perspect.* 1997 June; 105 (Suppl 4): 977-979. Oral perillyl alcohol has been used in a recent phase I trial sponsored by the National Cancer Institute. Although oral perillyl alcohol did not induce severe adverse effects, it was generally poorly tolerated, mainly due to gastrointestinal side effects. In addition, its anti-cancer efficacy was limited. As a result, the use of oral perillyl alcohol was discontinued. Ripple et al. Phase I clinical and pharmacokinetic study of perillyl alcohol administered four times a day. *Clinical Cancer Res* 6: 390-6, 2000.

In order to minimize the gastrointestinal side effects of oral POH and to provide a means of delivering POH directly to the central nervous system, a nasal formulation of POH (see below) for direct intranasal delivery of POH to malignant brain tumors was studied by Dr. Clovis Fonseca at the Fluminese University in Brazil. Da Fonseca, et al. Anaplastic oligodendroglioma responding favorably to intranasal delivery of perillyl alcohol: a case report and literature review, *Surgical Neurology* (2006) 66:611-615. This formulation of commercial grade POH combined with a solvent cocktail, has already been delivered to 150 patients with recurrent malignant gliomas, with minimal side effect and a six month 50% progression free survival rate. Da Fonseca et al. Correlation of tumor topography and peritumoral edema of recurrent malignant gliomas with therapeutic response to intranasal administration of perillyl alcohol. *Invest New Drugs* 2009, Jan. 13.

Commercial grade perillyl alcohol, with purities ranging from 85% to 96%, is typically purified from natural products, or by synthetically modifying natural products such as beta-pinene (extracted from pine trees). Inevitably, perillyl alcohol obtained through these routes is contaminated by its isomers and other impurities which have similar physicochemical properties, and, therefore, are extremely difficult to remove from perillyl alcohol by conventional purification methods such as fractional distillation or chromatography. Isomers of perillyl alcohol and other impurities may be potentially inhibitory towards the desired therapeutic properties of perillyl alcohol.

Consequently, there is still a need to prepare highly purified perillyl alcohol and use this material in the treatment of CNS cancers such as malignant gliomas, as well as other aggressive brain tumors. Purified perilly alcohol may be administered alone or in combination with other treatment methods including radiation, standard chemotherapy, and surgery. The administration can also be through various routes including intranasal, oral, oral-tracheal for pulmonary delivery, and transdermal.

SUMMARY OF THE INVENTION

The present invention provides for a process of purifying (S)-perillyl alcohol comprising the steps of: (a) derivatizing a mixture comprising (S)-perillyl alcohol to form a perillyl alcohol derivative, wherein the perillyl alcohol derivative has at least one property that allows it to be separated from the mixture; (b) separating the perillyl alcohol derivative from the mixture using the property for separation; (c) releasing the (S)-perillyl alcohol from the perillyl alcohol derivative from step (b); and, (d) isolating the (S)-perillyl alcohol from step (c). The (S)-perillyl alcohol has a purity greater than about 98.5% (w/w), greater than about 99.0% (w/w), or greater than about 99.5% (w/w). In certain embodiments, the mixture further comprises natural-product-derived or other impurities. The property of the perillyl alcohol derivative can be to form crystals, and the separation in step (b) can, therefore, be through crystallization. The separation in step (b) may also be through chromatography. The perillyl alcohol derivative can be a perillyl alcohol ester. In one embodiment, the perillyl alcohol ester is a benzoate ester, such as 3,5-dinitrobenzoate ester.

The invention also encompasses an (S)-perillyl alcohol, where the (S)-perillyl alcohol has a purity greater than about 98.5% (w/w), greater than about 99.0% (w/w), or greater than about 99.5% (w/w).

The invention further provides for a pharmaceutical composition comprising (S)-perillyl alcohol having a purity greater than about 98.5% (w/w). The (S)-perillyl alcohol may have a purity greater than about 98.5% (w/w). The pharmaceutical composition may contain from about 0.1% (w/w) to about 100% (w/w) (S)-perillyl alcohol. In addition, the pharmaceutical composition may comprise a chemotherapeutic agent, as well as at least one pharmaceutically acceptable excipient. The chemotherapeutic agent may be a DNA alkylating agent, a topoisomerase inhibitor, an endoplasmic reticulum stress inducing agent, a platinum compound, an antimetabolite, an enzyme inhibitor, a receptor antagonist, a therapeutic antibody, or a vaccine. In certain embodiments, the chemotherapeutic agent is dimethyl-celecoxib (DMC), irinotecan (CPT-11), temozolomide, or rolipram. The pharmaceutical composition can be administered alone, or may be administered before, during or after radiation, or before, during or after the administration of a chemotherapeutic agent. The routes of administration include inhalation, intranasal, oral, intravenous, subcutaneous and intramuscular injection. The pharmaceutical composition can be administered intranasally by an intranasal spray device, an atomizer, a nebulizer, a metered dose inhaler (MDI), a pressurized dose inhaler, an insufflator, an intranasal inhaler, a nasal spray bottle, a unit dose container, a pump, a dropper, a squeeze bottle, or a bi-directional device. The pharmaceutical composition may be administered intranasally in the form of a gel, an ointment, a nasal emulsion, a lotion, a cream, a nasal tampon, or a bioadhesive strip.

The present invention further provides for a method of treating cancer, comprising the step of delivering to a mammal a therapeutically effective amount of (S)-perillyl alcohol having a purity greater than about 98.5% (w/w). The (S)-perillyl alcohol may be admixed or coformulated with a therapeutic agent, for example, a chemotherapeutic agent. The cancer may be a tumor of the nervous system, such as a glioblastoma, or other tumors.

The present invention provides for an article of manufacture (e.g., a kit) comprising (S)-perillyl alcohol formulated for intranasal administration, and a device for intranasal administration of the (S)-perillyl alcohol, wherein the (S)-perillyl alcohol has a purity of greater than about 98.5% (w/w). The device may be an intranasal spray device, an atomizer, a nebulizer, a metered dose inhaler (MDI), a pressurized dose inhaler, an insufflator, an intranasal inhaler, a nasal spray bottle, a unit dose container, a pump, a dropper, a squeeze bottle, or a bi-directional device. The article of manufacture may further comprise printed matter which states the (S)-perillyl alcohol is to be used to treat cancer, such as glioblastoma. The printed matter may further state the (S)-perillyl alcohol is to be administered alone, or administered in combination with radiation, surgery or chemotherapeutic agents.

Also provided for is a method of inhibiting the growth of a cell, comprising the step of contacting the cell with an effective amount of (S)-perillyl alcohol having a purity greater than about 98.5% (w/w). The contacting may occur in vitro or in vivo. The cell may be a glioma cell, a meningioma cell, a pituitary adenoma cell, a lung cancer cell, a prostate cancer cell, a breast cancer cell, a hematopoietic cancer cell, a melanoma cell, or an ovarian cancer cell. The cell may be a temozolomide-resistant cell or a cancer stem cell.

The compositions and methods of the present invention may be used to decrease or inhibit angiogenesis. The present compositions and methods may decrease or inhibit production of pro-angiogenic cytokines, including, but not limited to, vascular endothelial growth factor (VEGF) and interleukin 8 (IL8).

The compositions and methods of the present invention may be used to increase paracellular permeability, for example, paracellular permeability of endothelial cells or epithelial cells. The present compositions and methods may be used to increase blood brain barrier permeability.

DETAILED DESCRIPTION OF THE INVENTION

Figure 1:
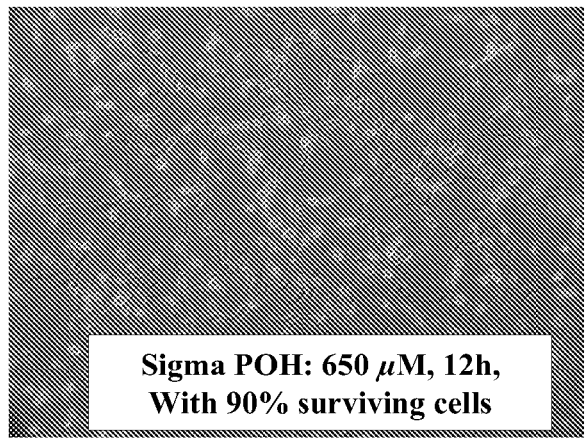
FIG. 1 shows light microscopic images demonstrating morphological changes of human malignant glioma cells A172 after being treated with purified (S)-perillyl alcohol having a purity greater than 98.5% (hereinafter "purified POH" or "purified (S)-perillyl alcohol"), as well as (S)-perillyl alcohol purchased from Sigma Chemicals having a purity of about 96%. Increased cytotoxicity is observed in the A172 glioma cells after treatment with purified (S)-perillyl alcohol (FIG. 1C) compared to commercial (S)-perillyl alcohol from Sigma Chemicals (FIGS. 1A and 1B).
Figure 1:
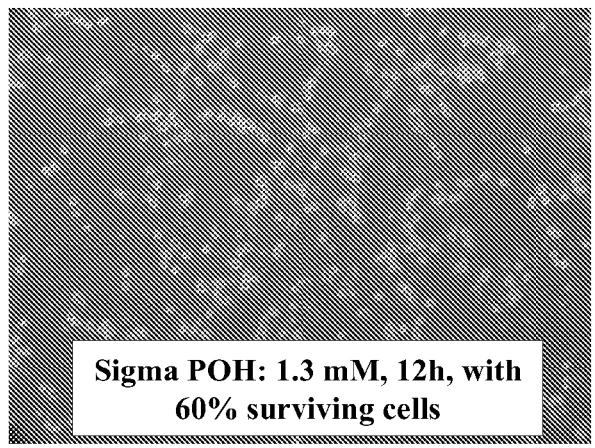
Figure 1:
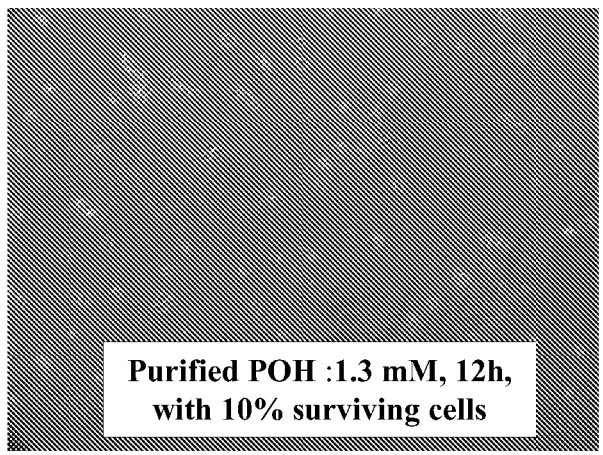

The present invention provides for methods of purifying perillyl alcohol from its isomers (including enantiomer) and other impurities that typically accompany perillyl alcohol when it is produced from natural products and/or synthetic sources. Perillyl alcohol may be purified by derivatizing perillyl alcohol to produce a crystalline derivative such as its 3,5-dinitrobenzoate ester. The perillyl alcohol derivative can then be separated from its accompanying contaminants (whether or not the contaminants are also present as derivatives or not) by suitable techniques, such as conventional crystallization, or preparative chromatography. The purified perillyl alcohol derivative can then be converted to perillyl alcohol which has a purity greater than about 98.5% (w/w). The purified perillyl alcohol may be administered to a subject alone, or may be co-administered together with other agents. For example, the purified perillyl alcohol may be used to sensitize a cancer patient to radiation or chemotherapy. Compared to commercially available (S)-perillyl alcohol, the purified (S)-perillyl alcohol demonstrates disproportionately enhanced activity in cellular assays and other therapeutic test models.

The present invention provides for a process of preparing a purified form of a monoterpene or sesquiterpene. The monoterpene (or sesquiterpene) is purified by the following steps: (a) derivatizing a mixture comprising monoterpene (or sesquiterpene) to form a monoterpene (or sesquiterpene) derivative, wherein the monoterpene (or sesquiterpene) derivative has at least one property that allows it to be separated from the mixture; (b) separating the monoterpene (or sesquiterpene) derivative from the mixture using the property for separation; (c) releasing the monoterpene (or sesquiterpene) from the monoterpene (or sesquiterpene) derivative from step (b); and, (d) isolating the monoterpene (or sesquiterpene) from step (c). The purified monoterpene (or sesquiterpene) may have a purity greater than about 98.5% (w/w), about 99.0% (w/w), or about 99.5% (w/w). In certain embodiments, the mixture further comprises natural-product-derived or other impurities.

The property of the monoterpene (or sesquiterpene) derivative can be to form crystals, and the separation in step (b) can, therefore, be through crystallization. The monoterpene (or sesquiterpene) is purified by the following steps: (a) derivatizing the monoterpene (or sesquiterpene) to form a monoterpene (or sesquiterpene) derivative; (b) crystallizing the monoterpene (or sesquiterpene) derivative; (c) separating the monoterpene (or sesquiterpene) derivative crystals of step (b); (d) converting the separated monoterpene (or sesquiterpene) derivative to monoterpene (or sesquiterpene); and (e) isolating the monoterpene (or sesquiterpene).

The separation of the monoterpene (or sesquiterpene) derivative from the mixture may also be through other suitable separation techniques known in the art, including, but not limited to, chromatography, adsorption, centrifugation, decantation, distillation, electrophoresis, evaporation, extraction, flotation, filtration, precipitation, sedimentation. Wikipedia—Separation Process. Retrieved on Feb. 11, 2010 from URL: http://en.wikipedia.org/wiki/Separation of mixtures. The property of the monoterpene (or sesquiterpene) derivative useful for separation of the derivative from the mixture can be any of its physicochemical properties that are different from that of the other components in the mixture. The physicochemical properties include, but are not limited to, solubility, polarity, partition coefficient, affinity, size, hydrodynamic diameter, and charge. The monoterpene (or sesquiterpene) derivative can be prepared where the derivative has at least one different property than that of its isomers, structural variants, or contaminants present in the starting material. The chromatography can be any suitable preparative chromatography, including, but not limited to, gas chromatography (GC), high pressure liquid chromatography (HPLC), affinity chromatography, ion exchange chromatography, size exclusion chromatography, and reversed-phase chromatography.

In one embodiment, the monoterpene may be (S)-perillyl alcohol, and the derivatization reaction can involve esterification. For example, (S)-perillyl alcohol may be prepared using a 3,5-dinitrobenzoate ester derivative.

The present invention further provides for a monoterpene (or sesquiterpene) composition having a purity of greater than about 98.5% (w/w), greater than about 99.0% (w/w), or greater than about 99.5% (w/w).

The purified monoterpene (or sesquiterpene) may be formulated into a pharmaceutical composition, where the monoterpene (or sesquiterpene) is present in amounts ranging from about 0.01% (w/w) to about 100% (w/w), from about 0.1% (w/w) to about 80% (w/w), from about 1% (w/w) to about 70% (w/w), from about 10% (w/w) to about 60% (w/w), or from about 0.1% (w/w) to about 20% (w/w). In addition, the pharmaceutical composition may contain a therapeutic agent, such as a chemotherapeutic agent. The therapeutic agent may be dissolved in perillyl alcohol. The present compositions can be administered alone, or may be co-administered together with radiation or another agent (e.g., a chemotherapeutic agent), to treat a disease such as cancer. Treatments may be sequential, with the monoterpene (or sesquiterpene) being administered before or after the administration of other agents. Alternatively, agents may be administered concurrently. The route of administration may vary, and can include, inhalation, intranasal, oral, transdermal, intravenous, subcutaneous or intramuscular injection.

The present invention also provides for a method of treating a disease such as cancer, comprising the step of delivering to a patient a therapeutically effective amount of a purified monoterpene (or sesquiterpene) prepared by the methods of the present invention.

The compositions of the present invention may contain one or more types of monoterpene (or sesquiterpene). Monoterpenes include terpenes that consist of two isoprene units and have the molecular formula $C_{10}H_{16}$. Monoterpenes may be linear (acyclic) or contain rings. Monoterpenoids, produced by biochemical modifications such as oxidation or rearrangement of monoterpenes, and pharmaceutically acceptable salts of monoterpenes or monoterpenoids, are also encompassed by the present invention. Examples of monoterpenes and monoterpenoids include, perillyl alcohol (S(−)) and R(+)), geranyl pyrophosphate, ocimene, myrcene, geraniol, citral, citronellol, citronellal, linalool, pinene, terpineol, terpinen, limonene, terpinenes, phellandrenes, terpinolene, terpinen-4-ol (or tea tree oil), pinene, terpineol, terpinen; the terpenoids such as p-cymene which is derived from monocyclic terpenes such as menthol, thymol and carvocrol; bicyclic monoterpenoids such as camphor, borneol and eucalyptol.

Monoterpenes may be distinguished by the structure of a carbon skeleton and may be grouped into acyclic monoterpenes (e.g., myrcene, (Z)- and (E)-ocimene, linalool, geraniol, nerol, citronellol, myrcenol, geranial, citral a, neral, citral b, citronellal, etc.), monocyclic monoterpenes (e.g., limonene, terpinene, phellandrene, terpinolene, menthol, carveol, etc.), bicyclic monoterpenes (e.g., pinene, myrtenol, myrtenal, verbanol, verbanon, pinocarveol, carene, sabinene, camphene, thujene, etc.) and tricyclic monoterpenes (e.g. tricyclene). See *Encyclopedia of Chemical Technology*, Fourth Edition, Volume 23, page 834-835.

Sesquiterpenes of the present invention include terpenes that consist of three isoprene units and have the molecular formula $C_{15}H_{24}$. Sesquiterpenes may be linear (acyclic) or contain rings. Sesquiterpenoids, produced by biochemical modifications such as oxidation or rearrangement of sesquiterpenes, are also encompassed by the present invention. Examples of sesquiterpenes include farnesol, farnesal, farnesylic acid and nerolidol.

The purified monoterpene (or sesquiterpene) is prepared using the derivatized monoterpene (or sesquiterpene), which may be separated from its accompanying contaminants (such as its isomers) by crystallization. The crystallization and purification may also enhance the chiral purity of the monoterpene (or sesquiterpene).

The derivatives of monoterpene (or sesquiterpene) include, but are not limited to, esters, alcohols, aldehydes and ketones of the monoterpene (or sesquiterpene). Monoterpene (or sesquiterpene) alcohols may be derivatized to esters, aldehydes or acids. The derivatives of monoterpene (or sesquiterpene) can be used to regenerate the monoterpene (or sesquiterpene) through chemical reactions known to a person skilled in the art. For example, an ester of a monoterpene (or sesquiterpene) can be hydrolyzed to generate the monoterpene (or sesquiterpene).

In one embodiment, a monoterpene (or sesquiterpene) is purified using an ester of the monoterpene (or sesquiterpene). The purification process includes the following steps: (a) derivatizing a monoterpene (or sesquiterpene) to produce an ester of the monoterpene (or sesquiterpene); (b) crystallizing the ester of the monoterpene (or sesquiterpene); (c) separating crystals of the ester of the monoterpene (or sesquiterpene) of step (b); (d) converting the ester of the monoterpene (or sesquiterpene) to the monoterpene (or sesquiterpene); and (e) isolating the monoterpene (or sesquiterpene).

Esters of the monoterpene (or sesquiterpene) alcohols of the present invention can be derived from an inorganic acid or an organic acid. Inorganic acids include, but are not limited to, phosphoric acid, sulfuric acid, and nitric acid. Organic acids include, but are not limited to, carboxylic acid such as benzoic acid, fatty acid, acetic acid and propionic acid. Examples of esters of monoterpene (or sesquiterpene) alcohols include, but are not limited to, carboxylic acid esters (such as benzoate esters, fatty acid esters (e.g., palmitate ester and linoleate ester), acetates, propionates (or propanoates), and formates), phosphates, sulfates, and carbamates (e.g., N,N-dimethylaminocarbonyl). Wikipedia—Ester. Retrieved from URL: http://en.wikipedia.org/wiki/Ester.

In one embodiment, the derivatives are benzoate esters including, but not limited to, 3,5-dinitrobenzoate ester, 4-nitrobenzoate ester, 3-nitrobenzoate ester, 4-chlorobenzoate ester, 3,4,5-trimethoxybenzoate ester and 4-methoxybenzoate ester, esters of hydroxybenzoic acid such as the methyl, ethyl, propyl, isopropyl, butyl, isobutyl, hexyl, heptyl and benzyl esters. (See, for example, Wikipedia—Benzoate ester http://commons.wikimedia.org/wiki/Category:Benzoate esters).

A specific example of a monoterpene that may be used in the present invention is perillyl alcohol (commonly abbreviated as POH). Perillyl alcohol compositions of the present invention can contain (S)-perillyl alcohol, (R)-perillyl alcohol, or a mixture of (S)-perillyl alcohol and (R)-perillyl alcohol.

Perillyl alcohol may be purified by the following steps: (a) derivatizing a mixture comprising perillyl alcohol to form a perillyl alcohol derivative, wherein the perillyl alcohol derivative has at least one property that allows it to be separated from the mixture; (b) separating the perillyl alcohol derivative from the mixture using the property for separation; (c) releasing the perillyl alcohol from the perillyl alcohol derivative from step (b); and (d) isolating the perillyl alcohol from step (c). In certain embodiments, the mixture further comprises natural-product-derived or other impurities.

Perillyl alcohol may be purified using the methods of the present invention with perillyl alcohol derivatives. The derivatives include, perillyl alcohol esters, perillic aldehyde, dihydroperillic acid, and perillic acid. The derivatives of perillyl alcohol may also include its oxidative and nucleophilic/electrophilic addition derivatives. U.S. Patent Publication No. 20090031455. U.S. Pat. Nos. 6,133,324 and 3,957,856. Many examples of derivatives of perillyl alcohol are reported in the chemistry literature (CAS Scifinder search output file, retrieved Jan. 25, 2010).

In a specific example, perillyl alcohol is purified by: (a) derivatizing perillyl alcohol to produce a perillyl alcohol ester; (b) crystallizing the perillyl alcohol ester; (c) separating the perillyl alcohol ester crystals of step (b) (e.g., from a mother liquor); (d) converting the separated perillyl alcohol ester to generate perillyl alcohol; and (e) isolating the perillyl alcohol. The derivative of perillyl alcohol can be used to regenerate the perillyl alcohol through chemical reactions known to a person skilled in the art. For example, an ester of perillyl alcohol, such as a 3,5-dinitrobenzoate ester, can be hydrolyzed to generate perillyl alcohol.

In certain embodiments, esters or ethers of perillyl alcohol may be prepared by reacting perillyl alcohol with acid chlorides or alkyl chlorides, the chemical structures of which are shown below.

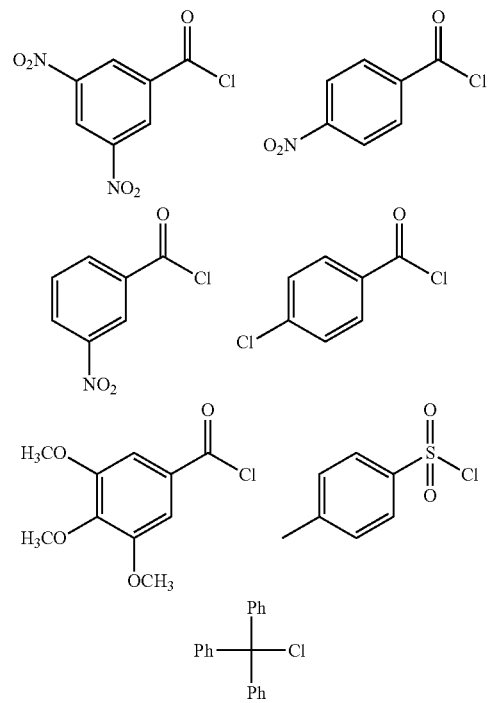

For the esterification reaction, the molar ratio of perillyl alcohol to acid chloride (or alkyl chloride) may range from about 1:1 to about 1:2, from about 1:1 to about 1:1.5, including, for example, about 1:1.05, about 1:1.1, about 1:1.2, about 1:1.3, or about 1:1.4. Suitable reaction solvents include, but are not limited to, dichloromethane, diethyl ether, diisopropyl ether, and methyl-t-butyl ether. The reaction may be performed at a temperature ranging from about −5° C. to about 50° C., or from about −5° C. to 25° C. Suitable bases that may be included in the reaction include, but are not limited to, organic bases, such as triethylamine, di-isopropylamine, N,N'-diisopropylethylamine, butylamine, sodium methoxide, potassium methoxide, and potassium-t-butoxide. The esters thus generated are 3,5-dinitrobenzoate ester, 4-nitrobenzoate ester, 3-nitrobenzoate ester, 4-chlorobenzoate ester, 3,4,5-trimethoxybenzoate ester, 4-methoxybenzoate ester and triphenylmethyl ester. The details of the chemical reactions are described in the Examples below.

The crystallizable monoterpene (or sesquiterpene) derivative may be purified by crystallization or preparative chromatography. Crystallization separates a product from a liquid feedstream, often in extremely pure form, by cooling the feedstream or adding precipitants which lower the solubility of the desired product so that it forms crystals. For crystallization to occur, the solution must be supersaturated. This means that the solution has to contain more dissolved solute entities than it would contain under the equilibrium (saturated solution). This can be achieved by various methods, such as 1) solution cooling; 2) addition of a second solvent to reduce the solubility of the solute (a technique known as antisolvent or drown-out); 3) chemical reaction; and 4) change in pH. Solvent evaporation, spherical crystallization, fractional crystallization, fractional freezing procedures, and other suitable methods can also be used. Mersmann, A. *Crystallization Technology Handbook*. Edition 2 (2001), published by CRC Press. Myerson et al. *Crystallization As a Separations Process* (ACS Symposium Series) (1990), published by American Chemical Society.

In a specific example, crystallization of 3,5-dinitrobenzoate ester of perillyl alcohol is carried out as follows. The aqueous layer containing 3,5-dinitrobenzoate ester is extracted with dichloromethane and washed with water. The organic layer which contains the 3,5-dinitrobenzoate ester is dried over sodium sulphate. The organic layer is then filtered and concentrated. The resulting residue is finally crystallized from a diisopropyl ether mother liquor. A mother liquor is the part of a liquid that is above the crystal solids, and, thus, can be separated from the crystals. The separation of the crystals from the mother liquor can be carried out using any suitable techniques, including, but not limited to, filtration (with or without the assistance of pressure and/or vacuum), centrifugation, and decantation.

Suitable solvents for crystallization of benzoate ester of perillyl alcohol include, but are not limited to, ketone solvents (such as acetone, methyl ethyl ketone, methyl isobutyl ketone, n-butanone, and t-butylketone); nitrile solvents (such as acetonitrile, and propionitrile); halogenated solvents (such as dichloromethane 1,2-dichloroethane, and chloroform); esters (such as ethyl acetate, n-propylacetate, isopropyl acetate, and t-butylacetate); ethers (such as diethyl ether, diisopropyl ether, methyl-t-butyl ether, tetrahydrofuran and 1,4-dioxane); hydrocarbon solvents (such as hexanes, cyclohexane, toluene and xylene); and mixtures thereof. In one embodiment, the solvent contains methyl-t-butyl ether. The dissolution of benzoate ester in methyl-t-butyl ether (7-10 volumes) may be performed at an elevated temperature, if required, to achieve the desired concentration. Further, an activated charcoal treatment may be performed to remove colored impurities or to reduce the content of heavy metals, if any, or to remove any extraneous matter from the solution containing benzoate ester. The crystallization from the resultant reaction mixture may be carried out by cooling the reaction mixture to a lower temperature of about 25° C. to about 0° C. Separation of the crystals may be carried out by removal of the solvent followed by cooling the reaction mixture. Solvent may be removed by suitable techniques including evaporation using a rotary evaporator, such as a Buchi rotavapor under vacuum. Crystals may be isolated from the reaction mixture by any conventional technique such as filtration by gravity or by suction. In one embodiment, the benzoate ester may be isolated by filtration and, if desired, may be further washed with a solvent. The benzoate ester may be dried by any of the conventional techniques such as drying in a tray dryer, vacuum dryer, or air oven. The drying may be carried out at a temperature of about 30° C. to about 60° C. in a vacuum oven.

The purity of the crystallizable monoterpene (or sesquiterpene) derivative, and therefore, the purity of the monoterpene (or sesquiterpene), may be further improved by recrystallization. Various techniques can be used, such as single-solvent recrystallization, multi-solvent recrystallization, hot filtration-recrystallization, as well as other suitable recrystallization techniques which are well known in the art. Wikipedia—Recrystallization. Retrieved from URL: http://en.wikipedia.org/wiki/Recrystallization (chemistry).

For example, U.S. Pat. No. Re. 32,241 describes an apparatus having a component crystallize on a cooled surface as material containing the component flows thereadown. U.S. Pat. No. 4,666,456 describes continuous partial crystallization of a compound from a liquid mixture in which the mixture is fed through a cascade of cooling sections. U.S. Pat. No. 5,127,921 provides a multi-stage recrystallization procedure including controlling reflux ratio conditions by regulating quantities of crystals and mother liquor reflux materials.

The purity of the perillyl alcohol may be greater than about 98.5% (w/w), greater than about 99% (w/w), greater than about 99.5% (w/w), or greater than about 99.9% (w/w).

In certain embodiments, the compounds of the invention contain one or more chiral centers. The term "purity" can also encompass chiral purity. The purity of a stereoisomer of a monoterpene (or sesquiterpene) refers to chemical purity and/or chiral purity of the stereoisomer. For example, the purity of (S)-perillyl alcohol can include both the chemical purity and the chiral purity of (S)-perillyl alcohol. The chiral purity of a stereoisomer of the monoterpene (or sesquiterpene) may be greater than about 98.5% (w/w), greater than about 99% (w/w), greater than about 99.5% (w/w), or greater than about 99.9% (w/w).

The chiral purity of (S)-perillyl alcohol may be greater than about 98.5% (w/w), greater than about 99% (w/w), greater than about 99.5% (w/w), or greater than about 99.9% (w/w). In certain embodiments, the specific optical rotation of (S)-perillyl alcohol of the present invention may range from −87.95° to −91.9°, when the specific optical rotation is measured at 22° C. with the sample concentration at 1 g/ml in MeOH (see Table 1 for examples of specific optical rotation of (S)-perillyl alcohol).

TABLE 1

Estimated chiral purity of perillyl alcohol samples based on optical rotation

| Vendor | Lot# | Quantity | Purity by Vendor (%) | Purity by Neonc analysis (%) GC (by area) | Specific optical rotation (C = 1, MeOH) | Sample description |
|---|---|---|---|---|---|---|
| Wako | ASK0744 | 5.0 g | 85 | 90.4 | −80.9° | Wako feed stock |
| Wako | KWH0744 (Neonc Sample# 12) | 400 g | 85 | 89.5 | −81.5° | Wako feed stock |
| Aldrich | MKAA4409 | 2 × 50 g | 96 | 95.0 | −88.7° | Aldrich lab sample |
| Aldrich | MKAA0552 | 100 g | •90 | 96.2 | −87.6° | Aldrich bulk representative sample |

TABLE 1-continued

Estimated chiral purity of perillyl alcohol samples based on optical rotation

| Vendor | Lot# | Quantity | Purity by Vendor (%) | Purity by Neonc analysis (%) GC (by area) | Specific optical rotation (C = 1, MeOH) | Sample description |
|---|---|---|---|---|---|---|
| Neonc | SGP-527-130 (Neonc Sample# 07) | 1.0 g | | 97.1 | −88.2° | Prepared from KWH0744 (single crystallized from diisopropyl ether) |
| Neonc | SGP-527-133 (Neonc Sample# 09) | 1.0 g | | 98.7 | −87.9° | Prepared from KWH0744 (Double recrystallized from diisopropyl ether then from 2-propanol) |
| Neonc | SGP-527-138 (Neonc Sample# 10) | 1.0 g | | 98.7 | −89.8° | Prepared from Aldrich MKAA0552 |
| Neonc | SGP-527-153 (Neonc Sample# 13) | 44.0 g | | 98.6 | −91.9° | Prepared from Wako KWH0744 |
| Neonc | SGP-527-155 (Neonc Sample# 14) | 46.0 g | | 98.6 | −91.7° | Prepared from Wako KWH0744 |

The purity of the monoterpene (or sesquiterpene) may be assayed by gas chromatography (GC) or high pressure liquid chromatography (HPLC). Other techniques for assaying the purity of monoterpene (or sesquiterpene) and for determining the presence of impurities include, but are not limited to, nuclear magnetic resonance (NMR) spectroscopy, mass spectrometry (MS), GC-MS, infrared spectroscopy (IR), and thin layer chromatography (TLC). WHO Specifications and Evaluations for Public Health Pesticides: Malathion, World Health Organization, 2003. Chiral purity can be assessed by chiral GC or measurement of optical rotation.

Alternatively, the monoterpene (or sesquiterpene) may be purified by methods other than crystallizing the derivates. For example, a monoterpene (or sesquiterpene) derivative can be prepared where the derivative has different physicochemical properties (e.g., solubility or polarity) than that of its isomers, structural variants, or contaminants present in the starting material. Accordingly, the monoterpene (or sesquiterpene) derivative can be separated from the monoterpene (or sesquiterpene) by suitable separation techniques known in the art, such as preparative chromatography.

The purified monoterpene (or sesquiterpene) may be stable after storage. For example, after storage at about 5° C. for at least 3 months, the present composition may contain greater than about 98.5% (w/w), greater than about 99% (w/w), greater than about 99.5% (w/w), or greater than about 99.9% (w/w) monoterpene (or sesquiterpene). After storage at 25° C. and 60% relative humidity for at least 3 months, the present composition can contain greater than about 98.5% (w/w), greater than about 99% (w/w), greater than about 99.5% (w/w), or greater than about 99.9% (w/w) monoterpene (or sesquiterpene).

The invention also provides for methods of using monoterpenes (or sesquiterpenes) to treat a disease, such as cancer or other nervous system disorders. Monoterpenes (or sesquiterpenes) may be administered alone, or in combination with radiation, surgery or chemotherapeutic agents. The monoterpene or sesquiterpene may also be co-administered with antiviral agents, anti-inflammatory agents or antibiotics. The agents may be administered concurrently or sequentially. Monoterpenes (or sesquiterpenes) can be administered before, during or after the administration of the other active agent(s).

The monoterpenes (or sesquiterpenes) may also be used as a solvent or a permeation enhancer to deliver a therapeutic agent to the lesion site. For example, monoterpenes (or sesquiterpenes) may be used as a solvent or a permeation enhancer to deliver chemotherapeutic agents to tumor cells. The monoterpene or sesquiterpene may also be used as a solvent for vaccines, which may be delivered through any suitable route, such as intranasally.

Monoterpenes (or sesquiterpenes) may be used for the treatment of nervous system cancers, such as a malignant glioma (e.g., astrocytoma, anaplastic astrocytoma, glioblastoma multiforme), retinoblastoma, pilocytic astrocytomas (grade I), meningiomas, metastatic brain tumors, neuroblastoma, pituitary adenomas, skull base meningiomas, and skull base cancer. As used herein, the term "nervous system tumors" refers to a condition in which a subject has a malignant proliferation of nervous system cells.

Cancers that can be treated by the present monoterpene (or sesquiterpene) compositions include, but are not limited to, lung cancer, ear, nose and throat cancer, leukemia, colon cancer, melanoma, pancreatic cancer, mammary cancer, prostate cancer, breast cancer, hematopoietic cancer, ovarian cancer, basal cell carcinoma, biliary tract cancer; bladder cancer; bone cancer; breast cancer; cervical cancer; choriocarcinoma; colon and rectum cancer; connective tissue cancer; cancer of the digestive system; endometrial cancer; esophageal cancer; eye cancer; cancer of the head and neck; gastric cancer; intra-epithelial neoplasm; kidney cancer; larynx cancer; leukemia including acute myeloid leukemia, acute lymphoid leukemia, chronic myeloid leukemia, chronic lymphoid leukemia; liver cancer; lymphoma including Hodgkin's and Non-Hodgkin's lymphoma; myeloma; fibroma, neuroblastoma; oral cavity cancer (e.g., lip, tongue, mouth, and pharynx); ovarian cancer; pancreatic cancer; prostate cancer; retinoblastoma; rhabdomyosarcoma; rectal cancer; renal cancer; cancer of the respiratory system; sarcoma; skin cancer; stomach cancer; testicular cancer; thyroid cancer; uterine cancer; cancer of the urinary system, as well as other carcinomas and sarcomas. U.S. Pat. No. 7,601,355.

The present invention also provides methods of treating CNS disorders, including, without limitation, primary degenerative neurological disorders such as Alzheimer's, Parkinson's, psychological disorders, psychosis and depression. Treatment may consist of the use of purified monoterpenes or sesquiterpenes alone or in combination with current medications used in the treatment of Parkinson's, Alzheimer's, or psychological disorders. For example, purified monoterpenes or sesquiterpenes may be used as a solvent for the inhalation of current medications used in the treatment of Parkinson's, Alzheimer's, or psychological disorders.

The monoterpene or sesquiterpene may be used in combination with radiation therapy. In one embodiment, the present invention provides for a method of treating tumor cells, such as malignant glioma cells, with radiation, where the cells are treated with an effective amount of a monoterpene, such as perillyl alcohol, and then exposed to radiation. Monoterpene treatment may be before, during and/or after radiation. For example, the monoterpene or sesquiterpene may be administered continuously beginning one week prior to the initiation of radiotherapy and continued for two weeks after the completion of radiotherapy. U.S. Pat. Nos. 5,587,402 and 5,602,184.

The present monoterpene or sesquiterpene may be used in combination with at least one therapeutic agents, including, but not limited to, chemotherapeutic agents, immunotherapeutic agents, and antibodies (e.g., monoclonal antibodies). The anti-cancer agents that may be used in combination with the purified monoterpene or sesquiterpene can have one or more of the following effects on cancer cells or the subject: cell death; decreased cell proliferation; decreased numbers of cells; inhibition of cell growth; apoptosis; necrosis; mitotic catastrophe; cell cycle arrest; decreased cell size; decreased cell division; decreased cell survival; decreased cell metabolism; markers of cell damage or cytotoxicity; indirect indicators of cell damage or cytotoxicity such as tumor shrinkage; improved survival of a subject; or disappearance of markers associated with undesirable, unwanted, or aberrant cell proliferation. U.S. Patent Publication No. 20080275057.

Also encompassed by the present invention are admixtures and/or coformulations of a monoterpene (or sesquiterpene) and at least one therapeutic agent, including, but not limited to, a chemotherapeutic agent.

Chemotherapeutic agents include, but are not limited to, DNA alkylating agents, topoisomerase inhibitors, endoplasmic reticulum stress inducing agents, a platinum compound, an antimetabolite, vincalkaloids, taxanes, epothilones, enzyme inhibitors, receptor antagonists, therapeutic antibodies, tyrosine kinase inhibitors, boron radiosensitizers (i.e. velcade), and chemotherapeutic combination therapies.

In one embodiment, the present invention provides for a method of treating tumor cells, such as malignant glioma cells, with chemotherapy, where the cells are treated with an effective amount of a monoterpene, such as perillyl alcohol, and then exposed to chemotherapy. Monoterpene treatment may be before, during and/or after chemotherapy.

DNA alkylating agents are well known in the art and are used to treat a variety of tumors. Non-limiting examples of DNA alkylating agents are nitrogen mustards, such as Mechlorethamine, Cyclophosphamide (Ifosfamide, Trofosfamide), Chlorambucil (Melphalan, Prednimustine), Bendamustine, Uramustine and Estramustine; nitrosoureas, such as Carmustine (BCNU), Lomustine (Semustine), Fotemustine, Nimustine, Ranimustine and Streptozocin; alkyl sulfonates, such as Busulfan (Mannosulfan, Treosulfan); Aziridines, such as Carboquone, ThioTEPA, Triaziquone, Triethylenemelamine; Hydrazines (Procarbazine); Triazenes such as Dacarbazine and Temozolomide; Altretamine and Mitobronitol.

Non-limiting examples of Topoisomerase I inhibitors include Campothecin derivatives including CPT-11 (irinotecan), SN-38, APC, NPC, campothecin, topotecan, exatecan mesylate, 9-nitrocamptothecin, 9-aminocamptothecin, lurtotecan, rubitecan, silatecan, gimatecan, diflomotecan, extatecan, BN-80927, DX-8951f, and MAG-CPT as decribed in Pommier Y. (2006) *Nat. Rev. Cancer* 6(10):789-802 and U.S. Patent Publication No. 200510250854; Protoberberine alkaloids and derivatives thereof including berberrubine and coralyne as described in Li et al. (2000) *Biochemistry* 39(24):7107-7116 and Gatto et al. (1996) *Cancer Res.* 15(12):2795-2800; Phenanthroline derivatives including Benzo[i]phenanthridine, Nitidine, and fagaronine as described in Makhey et al. (2003) *Bioorg. Med. Chem.* 11(8): 1809-1820; Terbenzimidazole and derivatives thereof as described in Xu (1998) *Biochemistry* 37(10):3558-3566; and Anthracycline derivatives including Doxorubicin, Daunorubicin, and Mitoxantrone as described in Foglesong et al. (1992) *Cancer Chemother. Pharmacol.* 30(2):123-125, Crow et al. (1994) *J. Med. Chem.* 37(19):31913194, and Crespi et al. (1986) *Biochem. Biophys. Res. Commun.* 136 (2):521-8. Topoisomerase II inhibitors include, but are not limited to Etoposide and Teniposide. Dual topoisomerase I and II inhibitors include, but are not limited to, Saintopin and other Naphthecenediones, DACA and other Acridine-4-Carboxamindes, Intoplicine and other Benzopyridoindoles, TAS-I03 and other 7H-indeno[2,1-c]Quinoline-7-ones, Pyrazoloacridine, XR 11576 and other Benzophenazines, XR 5944 and other Dimeric compounds, 7-oxo-7H-dibenz[f,ij]Isoquinolines and 7-oxo-7H-benzo[e] Perimidines, and Anthracenyl-amino Acid Conjugates as described in Denny and Baguley (2003) *Curr. Top. Med. Chem.* 3(3):339-353. Some agents inhibit Topoisomerase II and have DNA intercalation activity such as, but not limited to, Anthracyclines (Aclarubicin, Daunorubicin, Doxorubicin, Epirubicin, Idarubicin, Amrubicin, Pirarubicin, Valrubicin, Zorubicin) and Antracenediones (Mitoxantrone and Pixantrone).

Examples of endoplasmic reticulum stress inducing agents include, but are not limited to, dimethyl-celecoxib (DMC), nelfinavir, celecoxib, and boron radiosensitizers (i.e. velcade (Bortezomib)).

Platinum based compound which is a subclass of DNA alkylating agents. Non-limiting examples of such agents include Carboplatin, Cisplatin, Nedaplatin, Oxaliplatin, Triplatin tetranitrate, Satraplatin, Aroplatin, Lobaplatin, and JM-216. (see McKeage et al. (1997) *J. Clin. Oncol.* 201: 1232-1237 and in general, CHEMOTHERAPY FOR GYNECOLOGICAL NEOPLASM, CURRENT THERAPY AND NOVEL APPROACHES, in the Series Basic and Clinical Oncology, Angioli et al. Eds., 2004).

"FOLFOX" is an abbreviation for a type of combination therapy that is used to treat colorectal cancer. It includes 5-FU, oxaliplatin and leucovorin. Information regarding this treatment is available on the National Cancer Institute's web site, cancer.gov, last accessed on Jan. 16, 2008.

"FOLFOX/BV" is an abbreviation for a type of combination therapy that is used to treat colorectal cancer. This therapy includes 5-FU, oxaliplatin, leucovorin and Bevacizumab. Furthennore, "XELOX/BV" is another combination therapy used to treat colorectal cancer, which includes the prodrug to 5-FU, known as Capecitabine (Xeloda) in combination with oxaliplatin and bevacizumab. Information regarding these treatments are available on the National Cancer Institute's web site, cancer.gov or from the National Comprehensive Cancer Network's web site, nccn.org, last accessed on May 27, 2008.

Non-limiting examples of antimetabolite agents include Folic acid based, i.e. dihydrofolate reductase inhibitors, such as Aminopterin, Methotrexate and Pemetrexed; thymidylate synthase inhibitors, such as Raltitrexed, Pemetrexed; Purine based, i.e. an adenosine deaminase inhibitor, such as Pentostatin, a thiopurine, such as Thioguanine and Mercaptopurine, a halogenated/ribonucleotide reductase inhibitor, such as Cladribine, Clofarabine, Fludarabine, or a guanine/guanosine: thiopurine, such as Thioguanine; or Pyrimidine based, i.e. cytosine/cytidine: hypomethylating agent, such as Azacitidine and Decitabine, a DNA polymerase inhibitor, such as Cytarabine, a ribonucleotide reductase inhibitor, such as Gemcitabine, or a thymine/thymidine: thymidylate synthase inhibitor, such as a Fluorouracil (5-FU). Equivalents to 5-FU include prodrugs, analogs and derivative thereof such as 5'-deoxy-5-fluorouridine (doxifluroidine), 1-tetrahydrofuranyl-5-fluorouracil (ftorafur), Capecitabine (Xeloda), S-I (MBMS-247616, consisting of tegafur and two modulators, a 5-chloro-2,4dihydroxypyridine and potassium oxonate), ralititrexed (tomudex), nolatrexed (Thymitaq, AG337), LY231514 and ZD9331, as described for example in Papamicheal (1999) The Oncologist 4:478-487.

Examples of vincalkaloids, include, but are not limited to Vinblastine, Vincristine, Vinflunine, Vindesine and Vinorelbine.

Examples of taxanes include, but are not limited to docetaxel, Larotaxel, Ortataxel, Paclitaxel and Tesetaxel. An example of an epothilone is iabepilone.

Examples of enzyme inhibitors include, but are not limited to farnesyltransferase inhibitors (Tipifamib); CDK inhibitor (Alvocidib, Seliciclib); proteasome inhibitor (Bortezomib); phosphodiesterase inhibitor (Anagrelide; rolipram); IMP dehydrogenase inhibitor (Tiazofurine); and lipoxygenase inhibitor (Masoprocol). Examples of receptor antagonists include, but are not limited to ERA (Atrasentan); retinoid X receptor (Bexarotene); and a sex steroid (Testolactone).

Examples of therapeutic antibodies include, but are not limited to anti-HER1/EGFR (Cetuximab, Panitumumab); Anti-HER2/neu (erbB2) receptor (Trastuzumab); Anti-EpCAM (Catumaxomab, Edrecolomab) Anti-VEGF-A (Bevacizumab); Anti-CD20 (Rituximab, Tositumomab, Ibritumomab); Anti-CD52 (Alemtuzumab); and Anti-CD33 (Gemtuzumab). U.S. Pat. Nos. 5,776,427 and 7,601,355.

Examples of tyrosine kinase inhibitors include, but are not limited to inhibitors to ErbB: HER1/EGFR (Erlotinib, Gefitinib, Lapatinib, Vandetanib, Sunitinib, Neratinib); HER2/neu (Lapatinib, Neratinib); RTK class III: C-kit (Axitinib, Sunitinib, Sorafenib), FLT3 (Lestaurtinib), PDGFR (Axitinib, Sunitinib, Sorafenib); and VEGFR (Vandetanib, Semaxanib, Cediranib, Axitinib, Sorafenib); bcr-abl (Imatinib, Nilotinib, Dasatinib); Src (Bosutinib) and Janus kinase 2 (Lestaurtinib).

Cetuximab is an example of an anti-EGFR antibody. It is a chimeric human/mouse monoclonal antibody that targets the epidermal growth factor receptor (EGFR). Biological equivalent antibodies are identified herein as modified antibodies and those which bind to the same epitope of the EGFR antigen and produce a substantially equivalent biological response such as, preventing ligand binding of the EGFR, preventing activation of the EGFR receptor and the blocking of the downstream signaling of the EGFR pathway resulting in disrupted cell growth.

"Lapatinib" (Tykerb®) is an dual EGFR and erbB-2 inhibitor. Lapatinib has been investigated as an anticancer monotherapy, as well as in combination with trastuzumab, capecitabine, letrozole, paclitaxel and FOLF1R1(irinotecan, 5-fluorouracil and leucovorin), in a number of clinical trials. It is currently in phase III testing for the oral treatment of metastatic breast, head and neck, lung, gastric, renal and bladder cancer. A chemical equivalent of lapatinib is a small molecule or compound that is a tyrosine kinase inhibitor (TKI) or alternatively a HER-1 inhibitor or a HER-2 inhibitor. Several TKIs have been found to have effective antitumor activity and have been approved or are in clinical trials. Examples of such include, but are not limited to Zactima (ZD6474), Iressa (gefitinib) and Tarceva (erlotinib), imatinib mesylate (STI571; Gleevec), erlotinib (OSI-1774; Tarceva), canertinib (CI 1033), semaxinib (SU5416), vatalanib (PTK787/ZK222584), sorafenib (BAY 43-9006), sutent (SUI 1248) and lefltmomide (SU101). A biological equivalent of lapatinib is a peptide, antibody or antibody derivative thereof that is a HER-1 inhibitor and/or a HER-2 inhibitor. Examples of such include but are not limited to the humanized antibody trastuzumab and Herceptin.

PTK/ZK is a "small" molecule tyrosine kinase inhibitor with broad specificity that targets all VEGF receptors (VEGFR), the platelet-derived growth factor (PDGF) receptor, c-KIT and c-Fms. Drevs (2003) Idrugs 6(8):787-794. PTK/ZK is a targeted drug that blocks angiogenesis and lymphangiogenesis by inhibiting the activity of all known receptors that bind VEGF including VEGFR-I (Flt-1), VEGFR-2 (KDR/Flk-1) and VEGFR-3 (Flt-4). The chemical names of PTK/ZK are 1-[4-Chloroanilino]-4-[4-pyridylmethyl]phthalazine Succinate or 1-Phthalazinamine, N-(4-chlorophenyl)-4-(4-pyridinylmethyl)-butanedioate (1:1). Synonyms and analogs of PTK/TK are known as Vatalanib, CGP79787D, PTK787/ZK 222584, CGP-79787, DE-00268, PTK-787, PTK787A, VEGFR-TK inhibitor, ZK 222584 and ZK.

Chemotherapeutic agents that can be used in combination with the purified monoterpenes or sesquiterpenes may also include amsacrine, Trabectedin, retinoids (Alitretinoin, Tretinoin), Arsenic trioxide, asparagine depleter Asparaginase/Pegaspargase), Celecoxib, Demecolcine, Elesclomol, Elsamitrucin, Etoglucid, Lonidamine, Lucanthone, Mitoguazone, Mitotane, Oblimersen, Temsirolimus, and Vorinostat.

The compositions and methods of the present invention may be used to decrease the level of the Ras protein. The Ras family is a protein family of small GTPases that are involved in cellular signal transduction. Activation of Ras signaling causes cell growth, differentiation and survival. Mtations in ras genes can permanently activate it and cause inappropriate transmission inside the cell even in the absence of extracellular signals. Because these signals result in cell growth and division, dysregulated Ras signaling can ultimately lead to oncogenesis and cancer. Activating mutations in Ras are found in 20-25% of all human tumors and up to 90% in specific tumor types. Goodsell D S (1999). Downward J., "The molecular perspective: the ras oncogene". *Oncologist* 4 (3): 263-4. (January 2003). "Targeting RAS signalling pathways in cancer therapy". *Nat. Rev. Cancer* 3 (1): 11-22. Ras family members include, but are not limited to, HRAS; KRAS; NRAS; DIRAS1; DIRAS2; DIRAS3; ERAS; GEM; MRAS; NKIRAS1; NKIRAS2; NRAS; RALA; RALB; RAP1A; RAP1B; RAP2A; RAP2B; RAP2C; RASD1; RASD2; RASL10A; RASL10B; RASL11A; RASL11B; RASL12; REM1; REM2; RERG; RERGL; RRAD; RRAS; and RRAS. Wennerberg K, Rossman K L, Der C J (March 2005). "The Ras superfamily at a glance". *J. Cell. Sci.* 118 (Pt 5): 843-6.

The compositions and methods of the present invention may be used to increase paracellular permeability, for example, paracellular permeability of endothelial cells or epithelial cells. The present compositions and methods may be used to increase blood brain barrier permeability.

The compositions and methods of the present invention may be used to decrease or inhibit angiogenesis. The present compositions and methods may decrease or inhibit production of pro-angiogenic cytokines, including, but not limited to, vascular endothelial growth factor (VEGF) and interleukin 8 (IL8).

The purified monoterpenes or sesquiterpenes may be used in combination with angiogenesis inhibitors. Examples of angiogenesis inhibitors include, but are not limited to, angiostatin, angiozyme, antithrombin III, AG3340, VEGF inhibitors (e.g., anti-VEGF antibody), batimastat, bevacizumab (avastin), BMS-275291, CAI, 2C3, HuMV833 Canstatin, Captopril, carboxyamidotriazole, cartilage derived inhibitor (CDI), CC-5013, 6-O-(chloroacetyl-carbonyl)-fumagillol, COL-3, combretastatin, combretastatin A4 Phosphate, Dalteparin, EMD 121974 (Cilengitide), endostatin, erlotinib, gefitinib (Iressa), genistein, halofuginone hydrobromide, Id1, Id3, IM862, imatinib mesylate, IMC-IC11 Inducible protein 10, interferon-alpha, interleukin 12, lavendustin A, LY317615 or AE-941, marimastat, mspin, medroxpregesterone acetate, Meth-1, Meth-2, 2-methoxyestradiol (2-ME), neovastat, oteopontin cleaved product, PEX, pigment epithelium growth factor (PEGF), platelet factor 4, prolactin fragment, proliferin-related protein (PRP), PTK787/ZK 222584, ZD6474, recombinant human platelet factor 4 (rPF4), restin, squalamine, SU5416, SU6668, SU11248 suramin, Taxol, Tecogalan, thalidomide, thrombospondin, TNP-470, troponin-1, vasostatin, VEG1, VEGF-Trap, and ZD6474.

Non-limiting examples of angiogenesis inhibitors also include, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, pentosan polysulfate, angiotensin II antagonists, cyclooxygenase inhibitors (including non-steroidal anti-inflammatory drugs (NSAIDs) such as aspirin and ibuprofen, as well as selective cyclooxygenase-2 inhibitors such as celecoxib and rofecoxib), and steroidal anti-inflammatories (such as corticosteroids, mineralocorticoids, dexamethasone, prednisone, prednisolone, methylpred, betamethasone).

Other therapeutic agents that modulate or inhibit angiogenesis and may also be used in combination with the compounds of the instant invention include agents that modulate or inhibit the coagulation and fibrinolysis systems. Examples of such agents that modulate or inhibit the coagulation and fibrinolysis pathways include, but are not limited to, heparin, low molecular weight heparins and carboxypeptidase U inhibitors (also known as inhibitors of active thrombin activatable fibrinolysis inhibitor [TAFIa]). U.S. Patent Publication No. 20090328239. U.S. Pat. No. 7,638,549.

The present invention also provides a method of improving immunomodulatory therapy responses comprising the steps of exposing cells to an effective amount of a monoterpene or sisquiterpene, such as perillyl alcohol, before or during immunomodulatory treatment. Preferred immunomodulatory agents are cytokines, such interleukins, lymphokines, monokines, interfereons and chemokines.

This invention further provides for compositions where the purified monoterpene (or sesquiterpene) functions as a solvent or a permeation enhancer. In one aspect, the monoterpene is perillyl alcohol. Examples of the therapeutic agents are provided infra The composition may further comprise one or more pharmaceutically acceptable carriers, co-solvents, or other permeation enhancers.

In one embodiment, the composition contains the following components: a therapeutic agent; at least about 0.03% (v/v) of a monoterpene (or sesquiterpene) such as perillyl alcohol; at least about 2.6% (v/v) of a co-solvent which can be 1.3% (v/v) of a polyol such as glycerol or an equivalent thereof; and at least about 1.3% (v/v) of ethanol or an equivalent thereof.

Other permeation enhancers that may be used together with the purified monoterpene (or sesquiterpene) include, but are not limited to, fatty acid esters of glycerin, such as capric, caprylic, dodecyl, oleic acids; fatty acid esters of isosorbide, sucrose, polyethylene glycol; caproyllactylic acid; laureth-2; laureth-2 acetate; laureth-2 benzoate; laureth-3 carboxylic acid; laureth-4; laureth-5 carboxylic acid; oleth-2; glyceryl pyroglutamate oleate; glyceryl oleate; N-lauroyl sarcosine; N-myristoyl sarcosine; Noctyl-2-pyrrolidone; lauraminopropionic acid; polypropylene glycol-4-laureth-2; polypropylene glycol-4-laureth-5dimethyl lauramide; lauramide diethanolamine (DEA), lauryl pyroglutamate (LP), glyceryl monolaurate (GML), glyceryl monocaprylate, glyceryl monocaprate, glyceryl monooleate (GMO) and sorbitan monolaurate. Polyols or ethanol may act as a permeation enhancer or co-solvent. See U.S. Pat. Nos. 5,785,991; 5,843,468; 5,882,676; and 6,004,578 for additional permeation enhancers.

Co-solvents are well-known in the art and include, without limitation, glycerol, polyethylene glycol (PEG), glycol, ethanol, methanol, propanol, isopropanol, butanol and the like.

The present composition may be administered by any method known in the art, including, without limitation, intranasal, oral, ocular, intraperitoneal, inhalation, intravenous, ICV, intracisternal injection or infusion, subcutaneous, implant, vaginal, sublingual, urethral (e.g., urethral suppository), subcutaneous, intramuscular, intravenous, transdermal, rectal, sub-lingual, mucosal, ophthalmic, spinal, intrathecal, intra-articular, intra-arterial, sub-arachinoid, bronchial and lymphatic administration. Topical formulation may be in the form of gel, ointment, cream, aerosol, etc; intranasal formulation can be delivered as a spray or in a drop; transdermal formulation may be administered via a transdermal patch or iontorphoresis; inhalation formulation can be delivered using a nebulizer or similar device. Compositions can also take the form of tablets, pills, capsules, semisolids, powders, sustained release formulations, solutions, suspensions, elixirs, aerosols, or any other appropriate compositions.

To prepare such pharmaceutical compositions, one or more of the purified monoterpenes (or sesquiterpenes) may be mixed with a pharmaceutical acceptable carrier, adjuvant and/or excipient, according to conventional pharmaceutical compounding techniques. Pharmaceutically acceptable carriers that can be used in the present compositions encompass any of the standard pharmaceutical carriers, such as a phosphate buffered saline solution, water, and emulsions, such as an oil/water or water/oil emulsion, and various types of wetting agents. The compositions can additionally contain solid pharmaceutical excipients such as starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Liquid carriers, particularly for injectable solutions, include water, saline, aqueous dextrose, and glycols. For examples of carriers, stabilizers and adjuvants, see *Remington's Pharmaceutical Sciences*, edited by E. W. Martin (Mack Publishing Company, 18th ed., 1990). The compositions also can include stabilizers and preservatives.

As used herein, the term "therapeutically effective amount" is an amount sufficient to treat a specified disorder or disease or alternatively to obtain a pharmacological response treating a disorder or disease. Methods of determining the most effective means and dosage of administration can vary with the composition used for therapy, the purpose of the therapy, the target cell being treated, and the subject being treated. Treatment dosages generally may be titrated to optimize safety and efficacy. Single or multiple administrations can be carried out with the dose level and pattern being selected by the treating physician. Suitable dosage formulations and methods of administering the agents can be readily determined by those of skill in the art. For example, the composition are administered at about 0.01 mg/kg to about 200 mg/kg, about 0.1 mg/kg to about 100 mg/kg, or about 0.5 mg/kg to about 50 mg/kg. When the compounds described herein are co-administered with another agent or therapy, the effective amount may be less than when the agent is used alone.

This invention also provides the compositions as described above for intranasal administration. As such, the compositions can further comprise a permeation enhancer. Southall et al. Developments in Nasal Drug Delivery, 2000. The purified monoterpene (or sesquiterpene) may be administered intranasally in a liquid form such as a solution, an emulsion, a suspension, drops, or in a solid form such as a powder, gel, or ointment. Devices to deliver intranasal medications are well known in the art. Nasal drug delivery can be carried out using devices including, but not limited to, intranasal inhalers, intranasal spray devices, atomizers, nasal spray bottles, unit dose containers, pumps, droppers, squeeze bottles, nebulizers, metered dose inhalers (MDI), pressurized dose inhalers, insufflators, and bi-directional devices. The nasal delivery device can be metered to administer an accurate effective dosage amount to the nasal cavity. The nasal delivery device can be for single unit delivery or multiple unit delivery. In a specific example, the ViaNase Electronic Atomizer from Kurve Technology (Bethell, Washington) can be used in this invention (http://www.kurvetech.com). The compounds of the present invention may also be delivered through a tube, a catheter, a syringe, a packtail, a pledget, a nasal tampon or by submucosal infusion. U.S. Patent Publication Nos. 20090326275, 20090291894, 20090281522 and 20090317377.

The purified monoterpene (or sesquiterpene) can be formulated as aerosols using standard procedures. The monoterpene (or sesquiterpene) may be formulated with or without solvents, and formulated with or without carriers. The formulation may be a solution, or may be an aqueous emulsion with one or more surfactants. For example, an aerosol spray may be generated from pressurized container with a suitable propellant such as, dichlorodifluoromethane, trichlorofluoromethane, dichlorotetrafluoroethane, hydrocarbons, compressed air, nitrogen, carbon dioxide, or other suitable gas. The dosage unit can be determined by providing a valve to deliver a metered amount. Pump spray dispensers can dispense a metered dose or a dose having a specific particle or droplet size. As used herein, the term "aerosol" refers to a suspension of fine solid particles or liquid solution droplets in a gas. Specifically, aerosol includes a gas-borne suspension of droplets of a monoterpene (or sesquiterpene), as may be produced in any suitable device, such as an MDI, a nebulizer, or a mist sprayer. Aerosol also includes a dry powder composition of the composition of the instant invention suspended in air or other carrier gas. Gonda (1990) *Critical Reviews in Therapeutic Drug Carrier Systems* 6:273-313. Raeburn et al., (1992) *Pharmacol. Toxicol. Methods* 27:143-159.

The purified monoterpene (or sesquiterpene) may be delivered to the nasal cavity as a powder in a form such as microspheres delivered by a nasal insufflator. The monoterpene (or sesquiterpene) may be absorbed to a solid surface, for example, a carrier. The powder or microspheres may be administered in a dry, air-dispensable form. The powder or microspheres may be stored in a container of the insufflator. Alternatively the powder or microspheres may be filled into a capsule, such as a gelatin capsule, or other single dose unit adapted for nasal administration.

The pharmaceutical composition can be delivered to the nasal cavity by direct placement of the composition in the nasal cavity, for example, in the form of a gel, an ointment, a nasal emulsion, a lotion, a cream, a nasal tampon, a dropper, or a bioadhesive strip. In certain embodiments, it can be desirable to prolong the residence time of the pharmaceutical composition in the nasal cavity, for example, to enhance absorption. Thus, the pharmaceutical composition can optionally be formulated with a bioadhesive polymer, a gum (e.g., xanthan gum), chitosan (e.g., highly purified cationic polysaccharide), pectin (or any carbohydrate that thickens like a gel or emulsifies when applied to nasal mucosa), a microsphere (e.g., starch, albumin, dextran, cyclodextrin), gelatin, a liposome, carbamer, polyvinyl alcohol, alginate, acacia, chitosans and/or cellulose (e.g., methyl or propyl; hydroxyl or carboxy; carboxymethyl or hydroxylpropyl).

The composition containing the purified monoterpene (or sesquiterpene) can be administered by oral inhalation into the respiratory tract, i.e., the lungs.

Typical delivery systems for inhalable agents include nebulizer inhalers, dry powder inhalers (DPI), and metered-dose inhalers (MDI).

Nebulizer devices produce a stream of high velocity air that causes a therapeutic agent in the form of liquid to spray as a mist. The therapeutic agent is formulated in a liquid form such as a solution or a suspension of particles of suitable size. In one embodiment, the particles are micronized. The term "micronized" is defined as having about 90% or more of the particles with a diameter of less than about 10 μm. Suitable nebulizer devices are provided commercially, for example, by PARI GmbH (Starnberg, Germany). Other nebulizer devices include Respimat (Boehringer Ingelheim) and those disclosed in, for example, U.S. Pat. Nos. 7,568,480 and 6,123,068, and WO 97/12687. The monoterpenes (or sesquiterpenes) can be formulated for use in a nebulizer device as an aqueous solution or as a liquid suspension.

DPI devices typically administer a therapeutic agent in the form of a free flowing powder that can be dispersed in a patient's air-stream during inspiration. DPI devices which use an external energy source may also be used in the present invention. In order to achieve a free flowing powder, the therapeutic agent can be formulated with a suitable excipient (e.g., lactose). A dry powder formulation can be made, for example, by combining dry lactose having a particle size between about 1 µm and 100 µm with micronized particles of the monoterpenes (or sesquiterpenes) and dry blending. Alternatively, the monoterpene can be formulated without excipients. The formulation is loaded into a dry powder dispenser, or into inhalation cartridges or capsules for use with a dry powder delivery device. Examples of DPI devices provided commercially include Diskhaler (GlaxoSmithKline, Research Triangle Park, N.C.) (see, e.g., U.S. Pat. No. 5,035,237); Diskus (GlaxoSmithKline) (see, e.g., U.S. Pat. No. 6,378,519; Turbuhaler (AstraZeneca, Wilmington, Del.) (see, e.g., U.S. Pat. No. 4,524,769); and Rotahaler (GlaxoSmithKline) (see, e.g., U.S. Pat. No. 4,353,365). Further examples of suitable DPI devices are described in U.S. Pat. Nos. 5,415,162, 5,239,993, and 5,715,810 and references therein.

MDI devices typically discharge a measured amount of therapeutic agent using compressed propellant gas. Formulations for MDI administration include a solution or suspension of active ingredient in a liquefied propellant. Examples of propellants include hydrofluoroalklanes (HFA), such as 1,1,1,2-tetrafluoroethane (HFA 134a) and 1,1,1,2,3,3,3-heptafluoro-n-propane, (HFA 227), and chlorofluorocarbons, such as $CCl_3F$. Additional components of HFA formulations for MDI administration include co-solvents, such as ethanol, pentane, water; and surfactants, such as sorbitan trioleate, oleic acid, lecithin, and glycerin. (See, for example, U.S. Pat. No. 5,225,183, EP 0717987, and WO 92/22286). The formulation is loaded into an aerosol canister, which forms a portion of an MDI device. Examples of MDI devices developed specifically for use with HFA propellants are provided in U.S. Pat. Nos. 6,006,745 and 6,143,227. For examples of processes of preparing suitable formulations and devices suitable for inhalation dosing see U.S. Pat. Nos. 6,268,533, 5,983,956, 5,874,063, and 6,221,398, and WO 99/53901, WO 00/61108, WO 99/55319 and WO 00/30614.

The monoterpenes (or sesquiterpenes) may be encapsulated in liposomes or microcapsules for delivery via inhalation. A liposome is a vesicle composed of a lipid bilayer membrane and an aqueous interior. The lipid membrane may be made of phospholipids, examples of which include phosphatidylcholine such as lecithin and lysolecithin; acidic phospholipids such as phosphatidylserine and phosphatidylglycerol; and sphingophospholipids such as phosphatidylethanolamine and sphingomyelin. Alternatively, cholesterol may be added. A microcapsule is a particle coated with a coating material. For example, the coating material may consist of a mixture of a film-forming polymer, a hydrophobic plasticizer, a surface activating agent or/and a lubricant nitrogen-containing polymer. U.S. Pat. Nos. 6,313,176 and 7,563,768.

Because of their ability to easily penetrate the dermis, monoterpenes may also be used alone or in combination with other chemotherapeutic agents via topical application for the treatment of localized cancers such as breast cancer or melanomas. As a transdermal delivery agent, monoterpenes may also be used in combination with narcotics or analgesics for transdermal delivery of pain medication.

This invention also provides the compositions as described above for ocular administration. As such, the compositions can further comprise a permeation enhancer. For ocular administration, the compositions described herein can be formulated as a solution, emulsion, suspension, etc. A variety of vehicles suitable for administering compounds to the eye are known in the art. Specific non-limiting examples are described in U.S. Pat. Nos. 6,261,547; 6,197,934; 6,056,950; 5,800,807; 5,776,445; 5,698,219; 5,521,222; 5,403,841; 5,077,033; 4,882,150; and 4,738,851.

The monoterpenes (or sesquiterpenes) can be given alone or in combination with other drugs for the treatment of the above diseases for a short or prolonged period of time. The present compositions can be administered to a mammal, preferably a human. Mammals include, but are not limited to, murines, rats, rabbit, simians, bovines, ovine, porcine, canines, feline, farm animals, sport animals, pets, equine, and primates.

The present invention further provides an article of manufacture (such as a kit) comprising the purified monoterpene (or sesquiterpene) formulated for intranasal administration, and a device for intranasal administration of the purified monoterpene (or sesquiterpene). The device for intranasal administration may be an intranasal spray device, an atomizer, a nebulizer, a metered dose inhaler (MDI), a pressurized dose inhaler, an insufflator, an intranasal inhaler, a nasal spray bottle, a unit dose container, a pump, a dropper, a squeeze bottle, or a bi-directional device. The article of manufacture can contain printed matter indicating purified monoterpene (or sesquiterpene) is to be used to treat a disease, such as cancer or other nervous system disorders. The printed matter may state that the monoterpenes (or sesquiterpenes) may be administered alone, or in combination with radiation, surgery or chemotherapeutic agents. The monoterpene or sesquiterpene may also be co-administered with antiviral agents, anti-inflammatory agents or antibiotics. The agents may be administered concurrently or sequentially.

The invention also provides a method for inhibiting the growth of a cell in vitro, ex vivo or in vivo, where a cell, such as a cancer cell, is contacted with an effective amount of the purified monoterpene (or sesquiterpene) as described herein. The present compositions and methods may be used to inhibit the growth of a cell that is resistant to a chemotherapeutic agent. For example, the present compositions and methods may be used to inhibit the growth of a temozolomide-resistant cell.

Pathological cells or tissue such as hyperproliferative cells or tissue may be treated by contacting the cells or tissue with an effective amount of a composition of this invention. The cells, such as cancer cells, can be primary cancer cells or can be cultured cells available from tissue banks such as the American Type Culture Collection (ATCC). The pathological cells can be cells of a systemic cancer, gliomas, meningiomas, pituitary adenomas, or a CNS metastasis from a systemic cancer, lung cancer, prostate cancer, breast cancer, hematopoietic cancer or ovarian cancer. The cells can be from a vertebrate, preferably a mammal, more preferably a human. U.S. Patent Publication No. 2004/0087651. Balassiano et al. (2002) *Intern. J. Mol. Med.* 10:785-788. Thorne, et al. (2004) *Neuroscience* 127:481-496. Fernandes, et al. (2005) *Oncology Reports* 13:943-947. Da Fonseca, et al. (2008) *Surgical Neurology* 70:259267. Da Fonseca, et al. (2008) *Arch. Immunol. Ther. Exp.* 56:267-276. Hashizume, et al. (2008) *Neuroncology* 10:112-120.

Cancer stem cells (CSCs) or tumour initiating cells are immature cells with stem cell features such as self-renewal. However, self-renewal is exacerbated in CSCs. Reya et al., Stem cells, cancer, and cancer stem cells. *Nature.* 2001, 414(6859):105-11. Additionally, glioma CSCs are resistant to chemo- and radio-therapy. Bao et al., Glioma stem cells promote radioresistance by preferential activation of the DNA damage response. *Nature.* 2006, 444(7120):756-60. Rich et al., Chemotherapy and cancer stem cells. *Cell Stem Cell.* 2007; 1(4):353-5. The present compositions and methods may be used to inhibit the growth of a cancer stem cell, including, but not limited to, a glioblastoma cancer stem cell.

In vitro efficacy of the present composition can be determined using methods well known in the art. For example, the cytoxicity of the present monoterpene (or sesquiterpene) and/or the therapeutic agents may be studied by MTT [3-(4,5-dimethylthiazol-2-yl)-2,5-diphenyl tetrazolium bromide] cytotoxicity assay. MTT assay is based on the principle of uptake of MTT, a tetrazolium salt, by metabolically active cells where it is metabolized into a blue colored formazon product, which can be read spectrometrically. *J. of Immunological Methods* 65: 55 63, 1983. The cytoxicity of the present monoterpene (or sesquiterpene) and/or the therapeutic agents may be studied by colony formation assay. Functional assays for inhibition of VEGF secretion and IL-8 secretion may be performed via ELISA. Cell cycle block by the present monoterpene (or sesquiterpene) and/or the therapeutic agents may be studied by standard propidium iodide (PI) staining and flow cytometry. Invasion inhibition may be studied by Boyden chambers. In this assay a layer of reconstituted basement membrane, Matrigel, is coated onto chemotaxis filters and acts as a barrier to the migration of cells in the Boyden chambers. Only cells with invasive capacity can cross the Matrigel barrier. Other assays include, but are not limited to cell viability assays, apoptosis assays, and morphological assays.

The following examples are presented for the purposes of illustration only and are not limiting the invention.

EXAMPLE 1

(S)-Perillyl Alcohol Purification via 3,5-Dinitrobenzoate Ester (S)-Perillyl alcohol can be purified directly from natural products, or be obtained by synthetic modification of natural products such as beta-pinene (extracted from pine trees) by oxidation and rearrangement (Scheme 1).

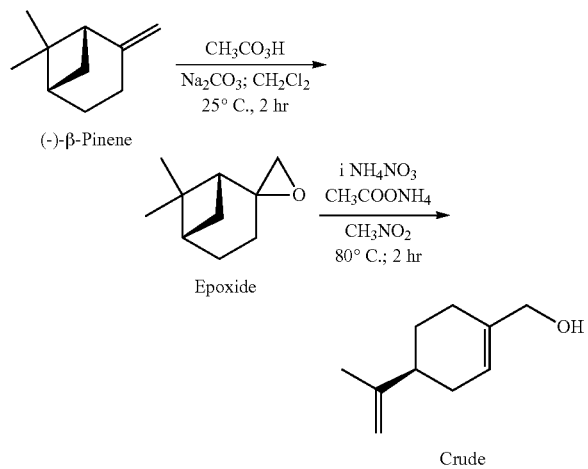

Such sources of (S)-perillyl alcohol are inevitably contaminated by isomers of the target compound which are very similar in physicochemical properties, and therefore, are difficult to remove by conventional methods of purification such as fractional distillation or chromatography.

In this Example, in order to purify (S)-perillyl alcohol from the contaminants that typically accompany it from natural product and/or synthetic sources, perillyl alcohol was first derivatized as its 3,5-dinitrobenzoate ester, which was separated from contaminants by conventional crystallization. Once the derivatized (S)-perillyl alcohol has been purified by crystallization it can then be hydrolyzed to recover the purified (S)-perillyl alcohol (Scheme 2). The purified (S)-perillyl alcohol prepared in this way has a purity greater than about 99%.

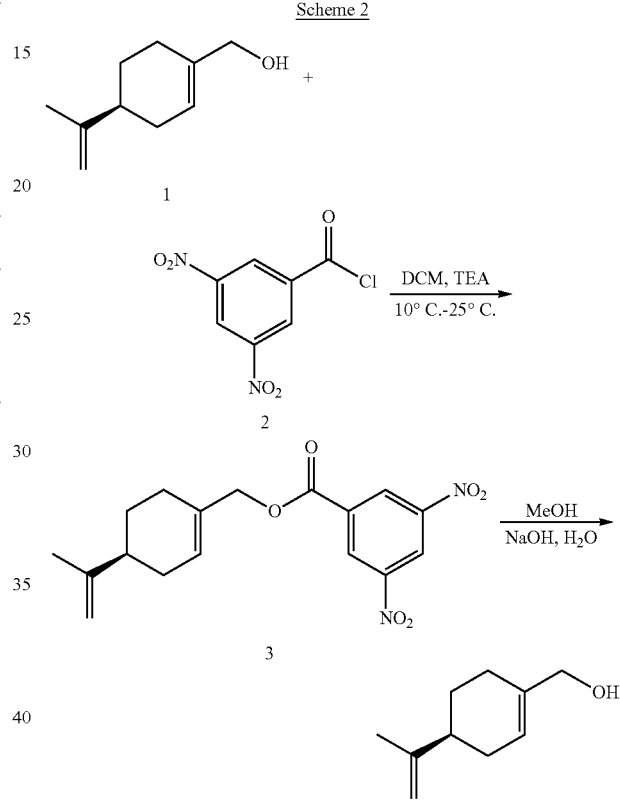

Synthesis of 3,5-Dinitrobenzoic acid 4-(S)-isopropenyl cyclohex-1-enylmethyl ester (Compound 3)

Triethyl amine (12.2 mL, 87.5 mmol) was added to a mixture of (S)-perillyl alcohol (1, 89.5% 10.0 g, 58.7 mmol) in dichloromethane (70 ml) over a period of 0.25 h while maintaining the temperature below 15° C. The reaction mixture was stirred for 30 min at room temperature. A solution of 3,5-dinitro benzoyl chloride (Compound 2, 14.23 g, 61.7 mmol) dissolved in dichloromethane (30 mL) was added over a period of 0.5 h while keeping the temperature below 15° C. The reaction mixture was allowed to warm to room temperature and then stirred for 3.0 h. The reaction mixture was quenched with water (75 mL) and the organic layer was separated. The aqueous layer was extracted with dichloromethane (50 mL). The combined organic layer was washed with water (2×100 mL) and dried over sodium sulphate (25 g). The filtered organic layer was concentrated and the resulting residue was crystallized from diisopropyl ether (200 mL) to get pure compound 3 (Weight: 14.45 g). The mother liquor was concentrated to half of its volume and 2.1 g was obtained as a second crop. (Total yield: 81.2%, Purity: 99.4% by HPLC.)

Hydrolysis of 3,5-Dinitrobenzoic acid 4-(S)-isopropenyl cyclohex-1-enylmethyl ester (Compound 3)

Aqueous sodium hydroxide (3.23 g, 80.0 mmol, dissolved in 28 mL of water) was added to an ice cold solution of 3,5-Dinitro-benzoic acid 4-isopropenyl-cyclohex-1-enylmethyl ester (14.0 g, 40.4 mmol) in methanol (140 mL) over a period of 0.25 h. The reaction mixture was allowed to warm to room temperature and then stirred for 3.0 h. The methanol was concentrated under vacuum and the resulting residue was suspended in water (60 mL) and extracted with ethyl acetate (2×100 mL). The organic layer was washed with water (2×100 mL) followed by brine (15%, 100 mL) and dried over sodium sulphate (30 g). The filtered organic layer was concentrated under vacuum to get pure (S)-perillyl alcohol (Weight: 5.84 g, Yield: 95% Purity: 99.4% by GC).

EXAMPLE 2

Synthesis of 3,5-Dinitrobenzoic Acid 4(S)-isopropenyl cyclohex-1-enylmethyl ester (Compound 3) and Purification by Preparative Chromatography Triethyl amine (5.3 mL, 38.0 mmol) was added to a mixture of (S)-perillyl alcohol (89.5% 5.0 g, 29.3 mmol) in dichloromethane (40 ml) over a period of 0.25 h while maintaining the temperature below 15° C. The reaction mixture was stirred for 30 min at room temperature. A solution of 3,5-dinitro benzoyl chloride (7.43 g, 32.2 mmol) dissolved in dichloromethane (15 mL) was added over a period of 0.5 h while maintain the temperature between 15-20° C. The reaction mixture was allowed to warm to room temperature and then stirred for 3.0 h. The reaction mixture was quenched with water (40 mL) and the organic layer was separated. The aqueous layer was extracted with dichloromethane (25 mL). The combined organic layer was washed with water (2×50 mL) and dried over sodium sulphate (20 g). The filtered organic layer was concentrated under vacuum to give a residue which was purified by column chromatography. Column dimensions were as follows: diameter: 2.5 cm, height: 30 cm, silica: 200 mesh. The column was eluted with hexanes:ethyl acetate (98:2, 200 mL) followed by hexanes: ethyl acetate (95:5). Based on TLC analysis of the fractions (solvent system; hexanes: ethyl acetate (90:10)), the hexanes: ethyl acetate (95:5) fractions were combined and concentrated under vacuum to give a solid. (Weight: 7.9 g Yield: 78%.)

EXAMPLE 2

Synthesis of 4-Nitrobenzoic acid 4(S)-isopropenyl cyclohex-1-enylmethyl Ester (Scheme 3)

Scheme 3

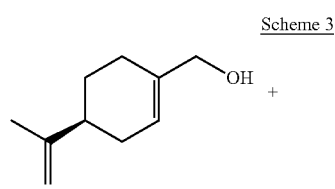

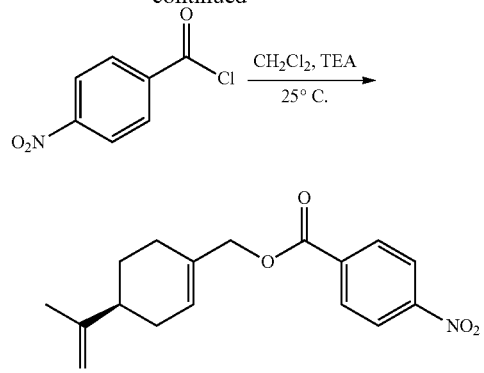

Triethyl amine (5.92 mL, 42.4 mmol) was added to a mixture of (S)-perillyl alcohol (5.0 g, 32.8 mmol) in dichloromethane (30 ml) over a period of 0.25 h while maintaining the temperature below 15° C. The reaction mixture was stirred for 30 min at room temperature. A solution of 4-nitrobenzoyl chloride (6.39 g, 34.4 mmol) dissolved in dichloromethane (30 mL) was added over a period of 0.5 h while keeping the temperature below 15° C. The reaction mixture was allowed to warm to room temperature and then stirred for 3.0 h. The reaction mixture was quenched with water (50 mL) and the organic layer was separated. The aqueous layer was extracted with dichloromethane (25 mL). The combined organic layer was washed with water (2×50 mL) and dried over sodium sulphate (20 g). The filtered organic layer was concentrated to give an oil (Weight: 8.9 g, yield: 90%).

EXAMPLE 3

Synthesis of 4-chlorobenzoic acid 4(S)-isopropenyl cyclohex-1-enylmethyl Ester (Scheme 4)

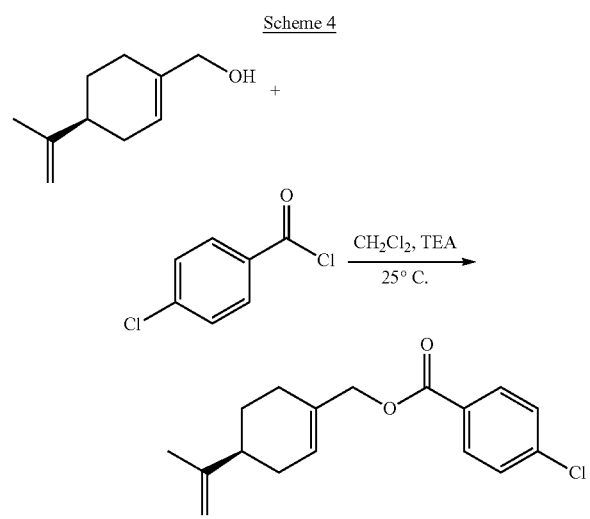

Triethyl amine (2.85 mL, 20.5 mmol) was added to a mixture of (S)-perillyl alcohol (2.5 g, 16.4 mmol) in dichloromethane (25 ml) over a period of 0.25 h while maintaining the temperature below 15° C. The reaction mixture was stirred for 30 min at room temperature. A solution of 4-chlorobenzoyl chloride (3.01 g, 17.2 mmol) dissolved in dichloromethane (10 mL) was added over a period of 0.5 h while keeping the temperature below 15° C. The reaction mixture was allowed to warm to room temperature and then stirred for 3.0 h. The reaction mixture was quenched with water (30 mL) and the organic layer was separated. The aqueous layer was extracted with dichloromethane (25 mL). The combined organic layer was washed with water (2×30 mL) and dried over sodium sulphate (15 g). The filtered organic layer was concentrated to give an oil (Weight: 3.8 g, yield: 81.7%).

EXAMPLE 4

Synthesis of 3,4,5-trimethoxybenzoic acid 4(S)-isopropenyl cyclohex-1-enylmethyl Ester (Scheme 5)

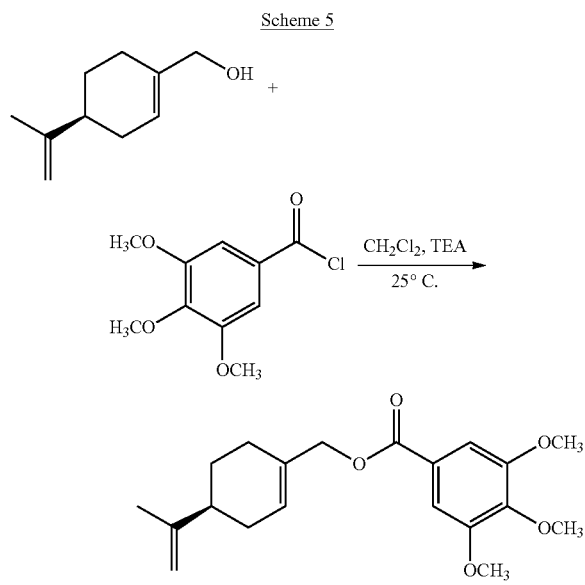

Triethyl amine (2.85 mL, 20.5 mmol) was added to a mixture of (S)-perillyl alcohol (2.5 g, 16.4 mmol) in dichloromethane (25 ml) over a period of 0.25 h while maintaining the temperature below 15° C. The reaction mixture was stirred for 30 min at room temperature. A solution of 3,4,5-trimethoxybenzoyl chloride (3.97 g, 17.2 mmol) dissolved in dichloromethane (10 mL) was added over a period of 0.5 h while keeping the temperature below 15° C. The reaction mixture was allowed to warm to room temperature and then stirred for 3.0 h. The reaction mixture was quenched with water (30 mL) and the organic layer was separated. The aqueous layer was extracted with dichloromethane (25 mL). The combined organic layer was washed with water (2×30 mL) and dried over sodium sulphate (15 g). The filtered organic layer was concentrated to give an oil (Weight: 4.8 g, yield: 84.6%).

EXAMPLE 5

Synthesis of 4-trimethoxybenzoic acid 4(S)-isopropenyl cyclohex-1-enylmethyl Ester (Scheme 6)

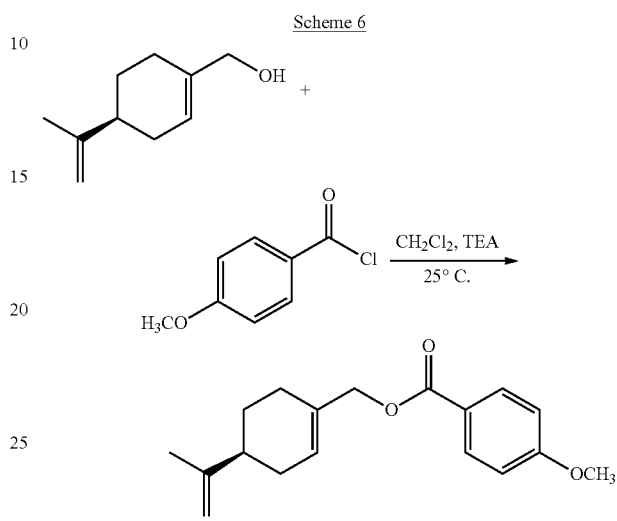

Triethyl amine (2.97 mL, 21.3 mmol) was added to a mixture of (S)-perillyl alcohol (2.5 g, 16.4 mmol) in dichloromethane (25 ml) over a period of 0.25 h while maintaining the temperature below 15° C. The reaction mixture was stirred for 30 min at room temperature. A solution of 4-methoxybenzoyl chloride (2.94 g, 17.2 mmol) dissolved in dichloromethane (10 mL) was added over a period of 0.5 h while keeping the temperature below 15° C. The reaction mixture was allowed to warm to room temperature and then stirred for 3.0 h. The reaction mixture was quenched with water (30 mL) and the organic layer was separated. The aqueous layer was extracted with dichloromethane (25 mL). The combined organic layer was washed with water (2×30 mL) and dried over sodium sulphate (15 g). The filtered organic layer was concentrated to give an oil (Weight: 4.1 g, yield: 87%).

EXAMPLE 6

Figure 2:
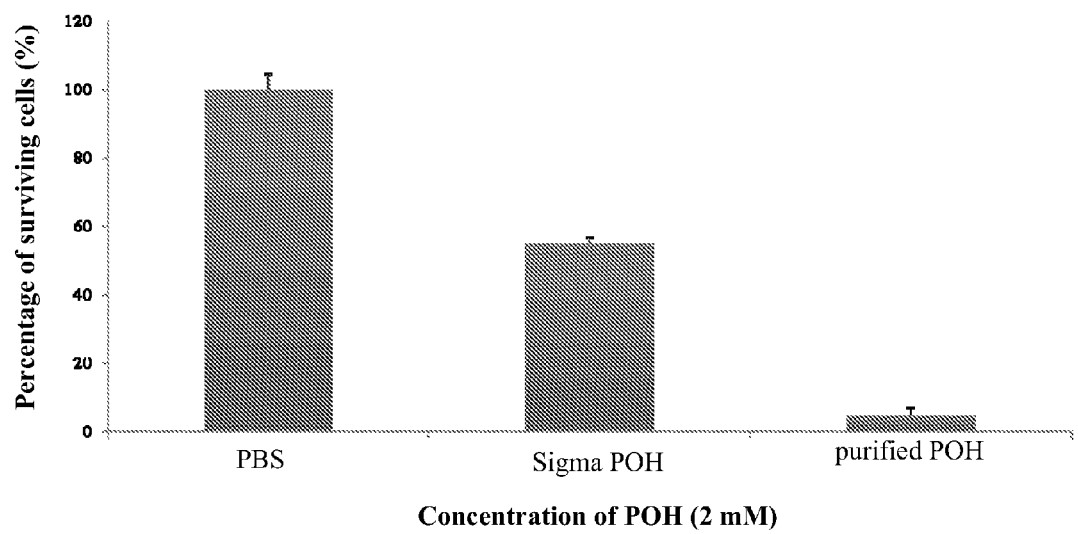
FIG. 2 shows the results of the MTT cytotoxicity assays performed on human malignant glioma cells U87 with purified (S)-perillyl alcohol having a purity greater than 98.5% compared to commercial grade (S)-perillyl alcohol from Sigma Chemicals having a purity of about 96%. Cells treated with phosphate-buffered saline (PBS) were used as control. The difference in cytotoxic effect between the purified (S)-perillyl alcohol and Sigma (S)-perillyl alcohol is much greater than the difference in (S)-perillyl alcohol purity. See details in the Examples below.

Functional Assays of Perillyl Alcohol In Vitro (S)-perillyl alcohol with greater than 98.5% purity was compared to commercial (S)-perillyl alcohol purchased from Sigma Chemicals (96% purity) at concentrations 650 µM or 1.3 mM using morphological assays, cytotoxicity assays with MTT to quantify cytotoxicity for dispersed cells, and colony formation assays (CFA). Morphological assays demonstrated that both the purified (S)-perillyl alcohol (greater than 98.5% purity) and the (S)-perillyl alcohol from Sigma (96% purity) had cytotoxicity activity on A172 malignant glioma cells within 12 hours. Both drugs induced cell rounding and detachment from the plate (FIG. 1). MTT assays showed that purified (S)-perillyl alcohol exhibited better cytotoxicity on U87 human malignant glioma cells than the less pure (S)-perillyl alcohol from Sigma (FIG. 2). The numeric difference in cytotoxic effect between the purified (S)-perillyl alcohol and Sigma (S)-perillyl alcohol is much greater than the numeric difference in (S)-perillyl alcohol purity. Compared to Sigma (S)-perillyl alcohol, the purity increase for the purified (S)-perillyl alcohol is about 2.6%; the cytotoxic property of the purified (S)-perillyl alcohol increased about 125%.

Figure 3A:
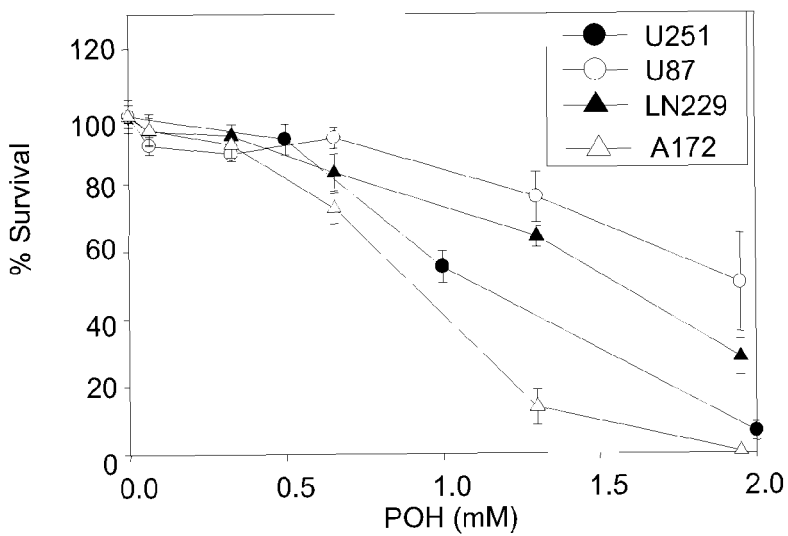
FIG. 3A shows the results of the MTT cytotoxicity assays demonstrating the efficacy of purified POH in killing U251, U87, LN299 and A172 human glioma cells.
Figure 3B:
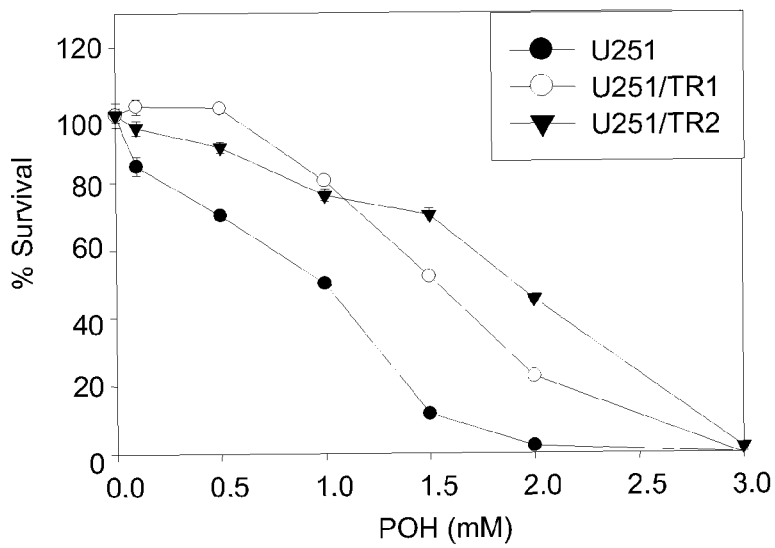
FIG. 3B shows the results of the MTT cytotoxicity assays demonstrating the efficacy of purified POH in killing U251 human glioma cells (temozolomide-sensitive) and U251 temozolomide-resistant cells. U251/TR1 and U251/TR2 refer to two temozolomide-resistant U251 cell lines.
Figure 3C:
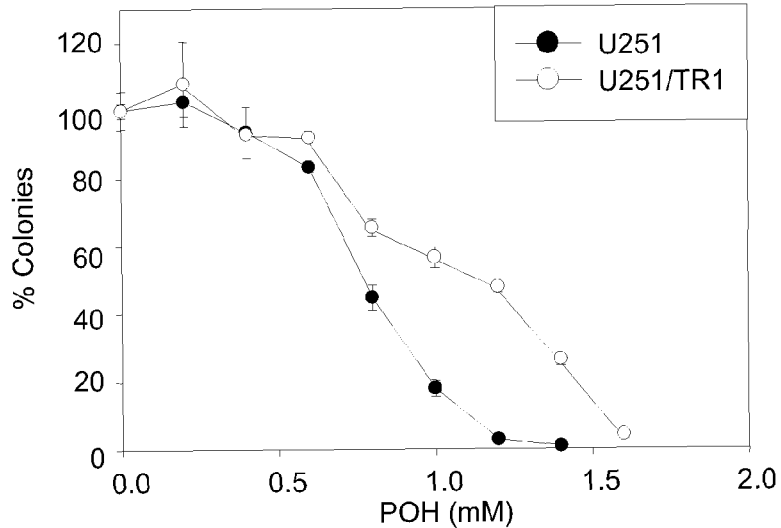
FIG. 3C shows the results of the colony formation assays performed on U251 human glioma cells (temozolomide-sensitive) and U251 temozolomide-resistant cells (U251/TR1).

FIG. 3A shows the results of the MTT cytotoxicity assays demonstrating the efficacy of purified POH in killing various kinds of human glioma cells, including U251, U87, LN299 and A172 cells. FIG. 3B shows the results of the MTT assays performed using temozolomide (TMZ) sensitive U251 glioma cells and temozolomide resistant U251 cell line (U251/TR1 and U251/TR2) over 24 hours using purified POH having a purity of about 98.7%. Purified POH is effective in killing both U251 human glioma cells (temozolomide-sensitive) and U251 temozolomide-resistant cells. The efficacy of purified POH on U251 temozolomide-resistant cells is also demonstrated by the colony formation assays shown in FIG. 3C.

POH has also been demonstrated to inhibit glioma invasion through a Boyden matrigel chamber, suggesting that it also has anti-invasion properties.

Figure 9:
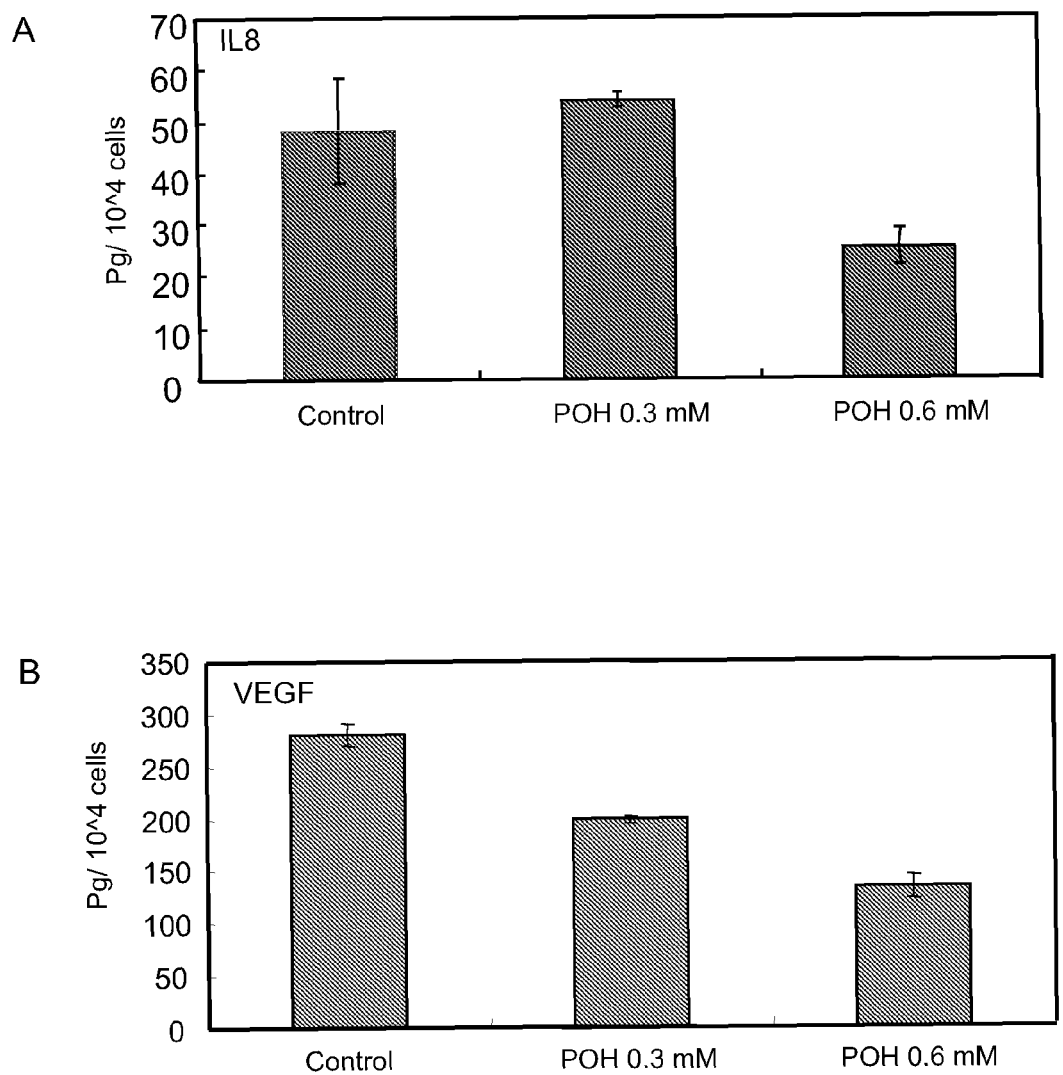
FIG. 9 shows the results of ELISA assays demonstrating that POH treatment decreases cytokine IL-8 (FIG. 9A) and VEGF secretion (FIG. 9B) in U87 human glioma cells. ELISA was performed after cells were treated with POH for 48 hours.

POH was found to be anti-angiogenic, as POH inhibited production of the pro-angiogenic cytokines vascular endothelial growth factor (VEGF) and interleukin 8 (IL8) by glioma cells. Functional assays for inhibition of VEGF secretion and IL-8 secretion by POH have been performed via ELISA assays (FIG. 9). POH has been shown to inhibit G1 cell cycle arrest. Pyrko et al. The unfolded protein response regulator GRP78/BiP as a novel target for increasing chemosensitivity in malignant gliomas. *Cancer Res* 67(20):9809-16, 2007. Cell cycle analysis after POH treatment will be performed using standard propidium iodide (PI) staining and flow cytometry. In addition, it may overcome the immunosuppressive functions of transforming growth factor beta-2 (TGFβ-2) secreted by glioma cells.

Figure 12:
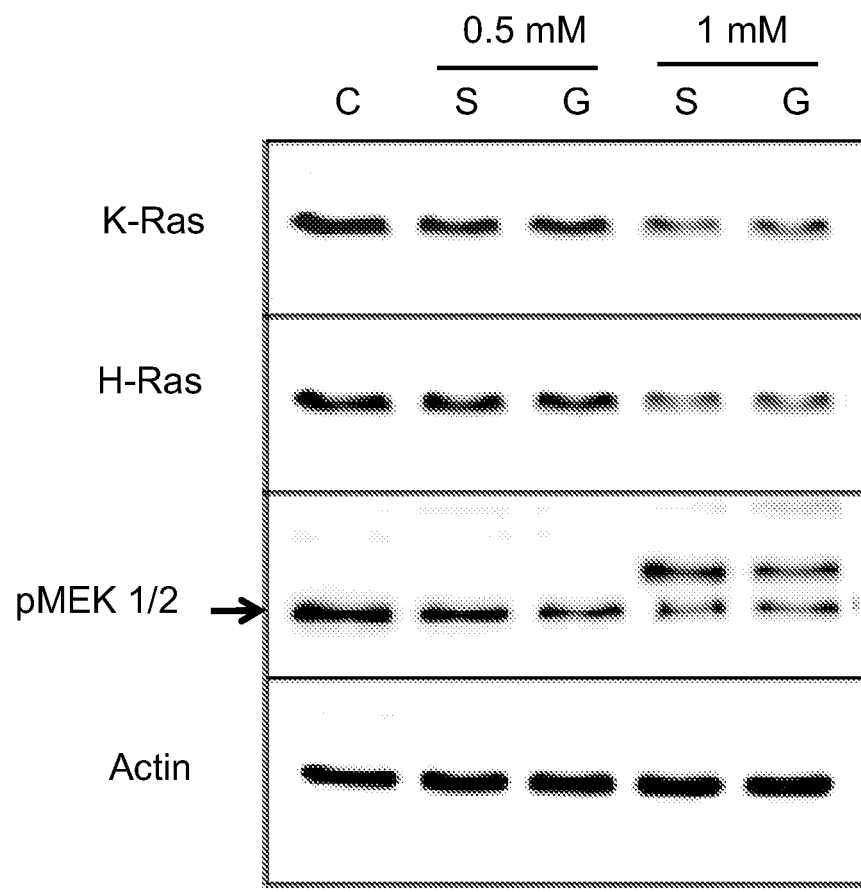
FIG. 12 shows Western blot performed after U251 glioma cells were treated for 24 hours with Sigma POH or purified POH. The results demonstrate that POH treatment decreases K-Ras and H-Ras expression.

U251 glioma cells were treated with Sigma POH or purified POH for 24 hours, then Western blot was performed. The results (FIG. 12) demonstrate that POH treatment decreased K-Ras and H-Ras expression.

EXAMPLE 7

Combination of POH and Radiation In Vitro

Figure 4A:
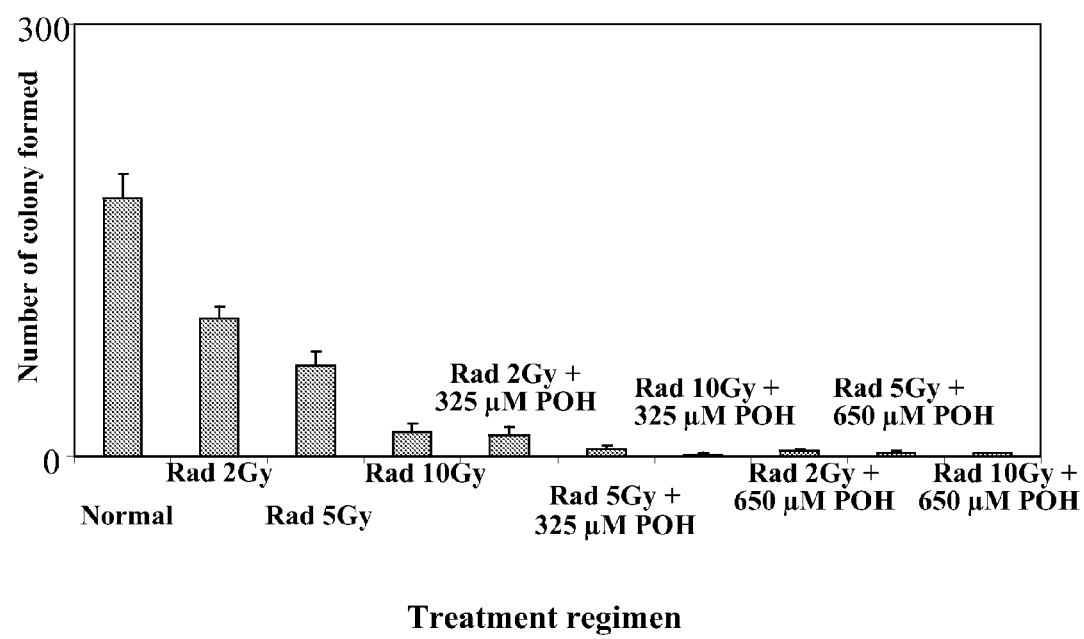
FIGS. 4A and 4B show the results of the colony formation assays performed on A172 (FIG. 4A), U251 human malignant glioma cells, and B16-F1 melanoma cells (FIG. 4B) treated with purified (S)-perillyl alcohol having a purity greater than 98.5% alone, radiation only, or purified (S)-perillyl alcohol plus radiation. In all three cell lines, synergistic cytotoxicity was achieved by the combination of purified (S)-perillyl alcohol plus radiation.
Figure 4B:
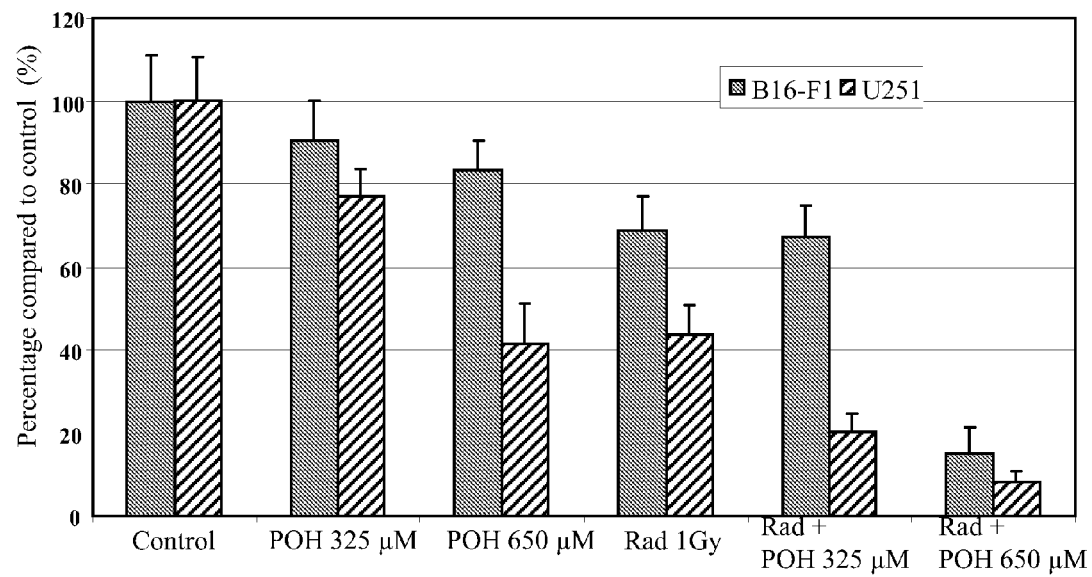

Purified (S)-POH having greater than 98.5% purity was assessed as a radiation sensitizer in human A172 glioma cells using the colony formation assays. Cells were treated with 325 µM or 650 µM POH prior to radiation at the doses of 2, 5 or 10 Grays (Gy). POH was shown to act synergistically with radiation in cell killing (FIG. 4A). This was confirmed for another human glioma cell line (U251) and also for a melanoma cell line (B16-F1) (FIG. 4B).

EXAMPLE 8

Combination of Perillyl Alcohol with Chemotherapeutic Agents In Vitro

Figure 5A:
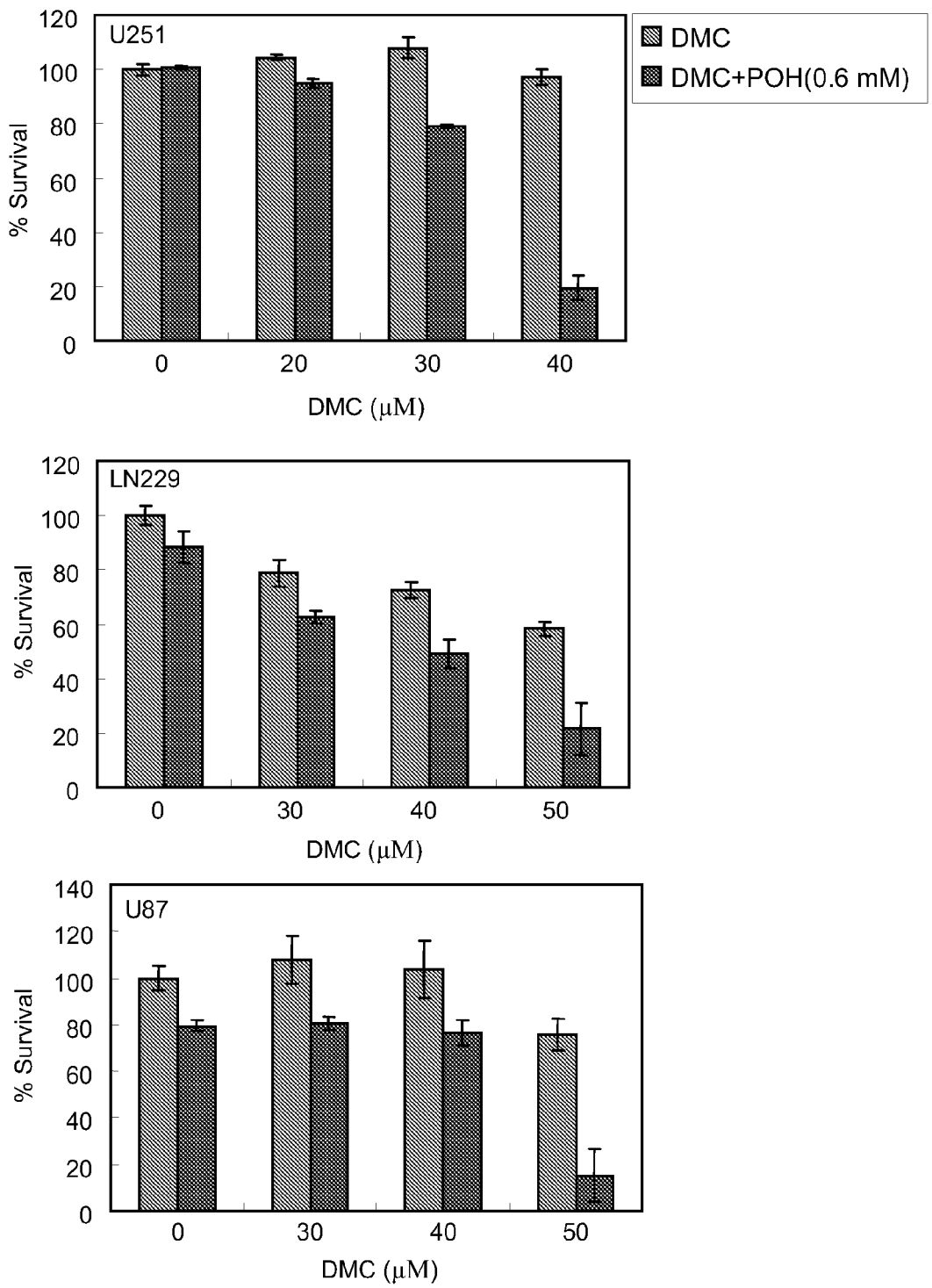
FIG. 5A shows the results of the MTT cytotoxicity assays demonstrating the efficacy of DMC or DMC combined with purified POH in killing U251, LN229 and U87 human glioma cells.
Figure 5B:
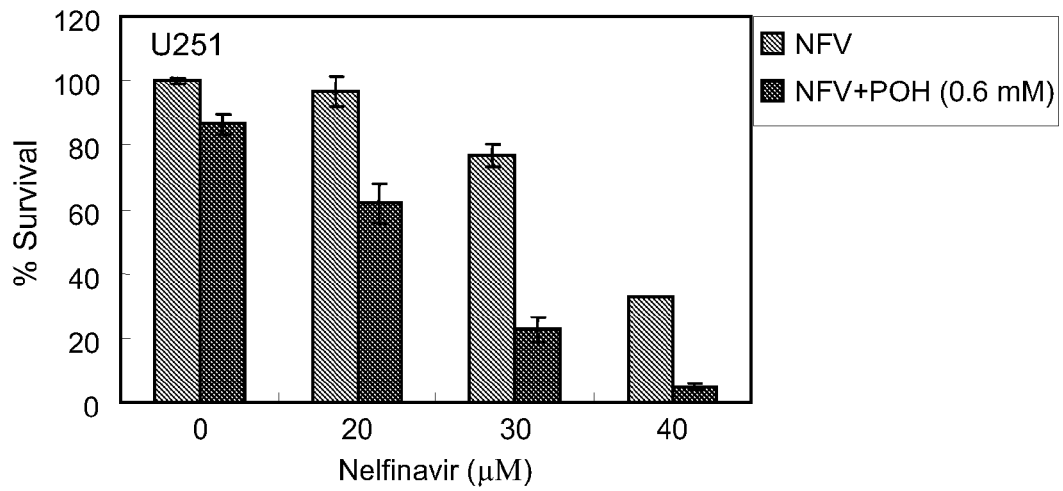
FIG. 5B shows the results of the MTT cytotoxicity assays demonstrating the efficacy of Nelfinavir (NFV) or NFV combined with purified POH in killing U251 human glioma cells.
Figure 5C:
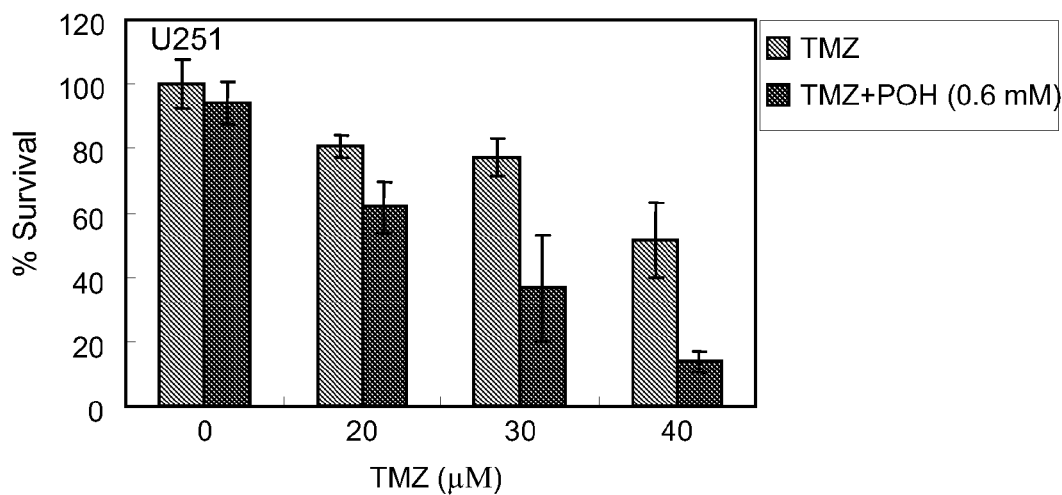
FIG. 5C shows the results of the MTT cytotoxicity assays demonstrating the efficacy of TMZ or TMZ combined with purified POH in killing U251 human glioma cells.

Cytotoxicity assays were carried out after cells were treated with POH in combination with temozolomide (TMZ), the standard alkylating agent used in the treatment of malignant gliomas. POH and TMZ was at least additive in cytotoxicity (or synergistic) (FIG. 5C). This effect was also seen in cell lines that were TMZ resistant.

Similarly, POH was at least additive (or synergistic) with dimethyl-celecoxib (DMC), determined by MTT cytotoxicity assays on various human glioma cell lines (FIG. 5A) and colony formation assays. POH was at least additive (or synergistic) with Nelfinavir (NFV), determined by MTT cytotoxicity assays (FIG. 5B). Pyrko et al. HIV-1 protease inhibitors nelfinavir and atazanavir induce malignant glioma death by triggering endoplasmic reticulum stress. *Cancer Res* 67(22): 10920-10928, 2007.

POH was also tested in combination with rolipram, a type IV phosphodiesterase which was demonstrated to cause differentiation and apoptosis in glioma cells. When cells were treated with rolipram alone, apoptosis occurred only after 48 hours post the addition of high concentrations of rolipram (e.g., 1 mM). Synergistic cell killing by rolipram and POH occurred within a much shorter time period, i.e., 6 hours after the addition of the drugs. Chen et al. The type IV phosphodiesterase inhibitor rolipram induces expression of the cell cycle inhibitors p21 Cip 1 and p27Kip1, resulting in growth inhibition, increased differentiation, and subsequent apoptosis of malignant A-12 glioma cells. *Cancer Biology & Therapy*, Vol. 1:3, 268-276, 2003.

EXAMPLE 9

POH Increases Paracellular Permeability and ER Stress

Figure 6:
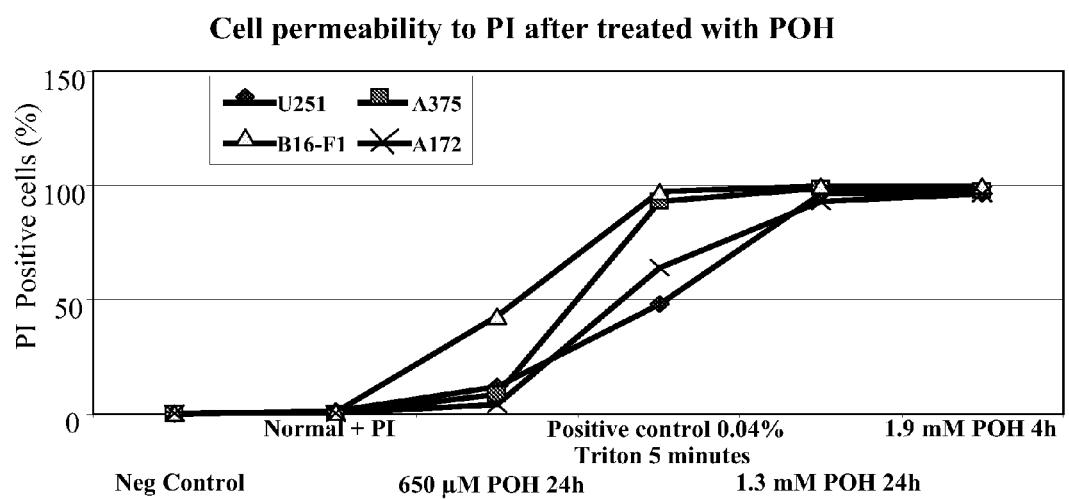
FIG. 6 shows the results of propidium iodide (PI) staining of A172, A375, U251 human malignant glioma cells and B16-F1 melanoma cells after being treated with purified (S)-perillyl alcohol having a purity greater than 98.5%, demonstrating that (S)-perillyl alcohol increases paracellular permeability.

FIG. 6 shows the results of propidium iodide (PI) staining of A172, A375, U251 human malignant glioma cells, and B16-F1 melanoma cells. 650 µM POH having a purity greater than 98.5% increased paracellular permeability to a greater extent than 0.04% Triton X, the positive control.

Figure 7A:
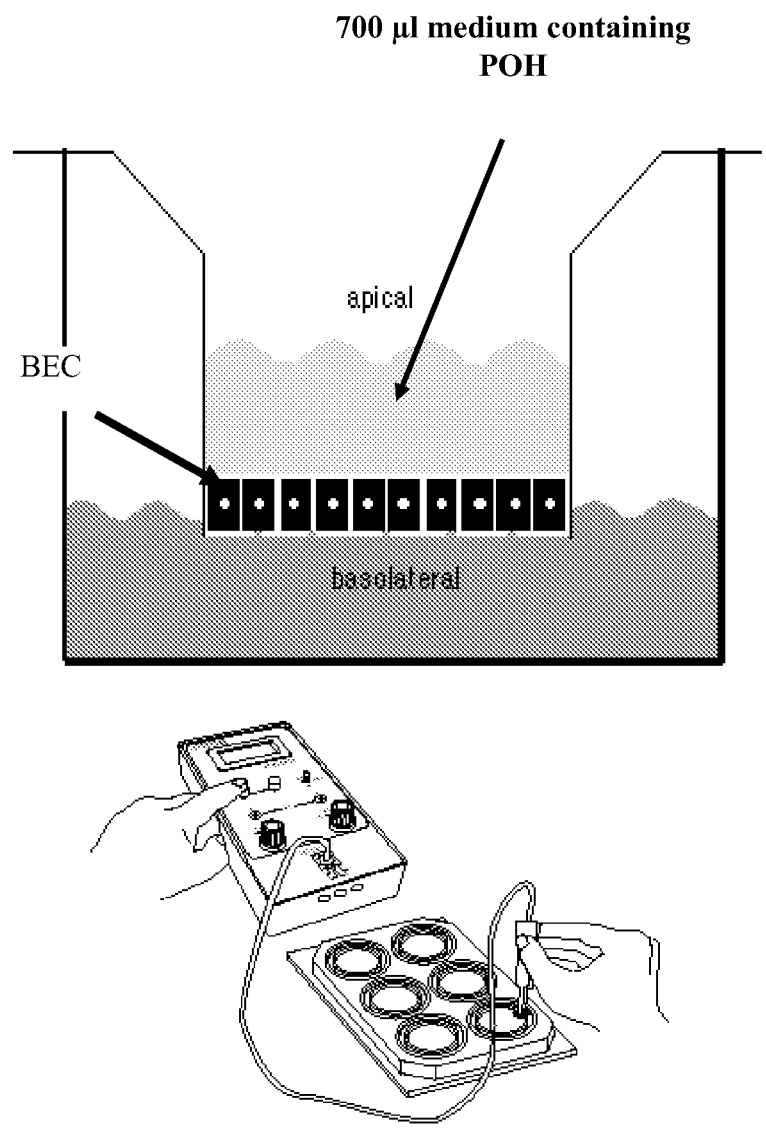
FIG. 7A shows the experimental scheme of the transepithelial electrical resistance (TEER) measurement to assess paracellular permeability.
Figure 7B:
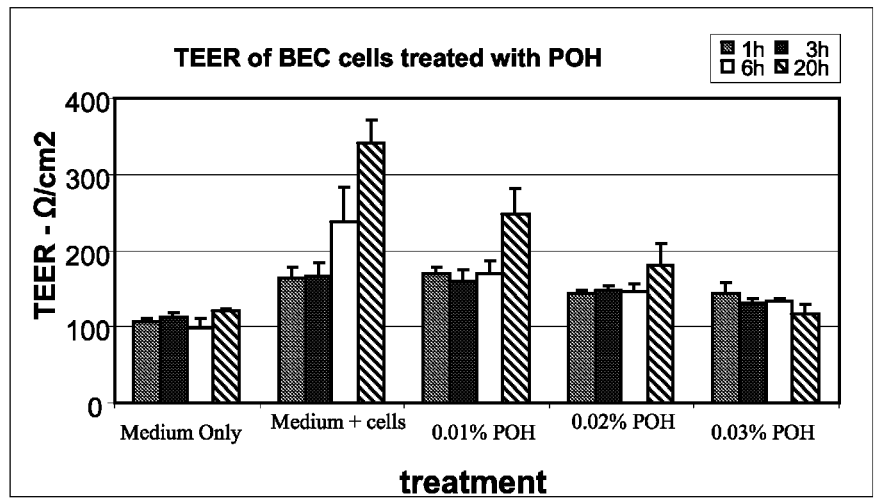
FIG. 7B shows that (S)-perillyl alcohol decreases the TEER, corresponding to an increase in paracellular permeability. In these experiments, brain endothelial cells (BECs) were used as an in vitro model of blood brain barrier. The increase in TEER in each group over time corresponds to increased confluency of the cells in culture. TEER decreased when cells were treated by 0.03% POH for 20 hours compared to medium only, 0.01% POH treatment, and 0.02% POH treatment.

Transepithelial electrical resistance (TEER) assays were performed assessing the ability of POH to increase paracellular permeability (FIG. 7A). In these experiments, brain endothelial cells (BECs) were used as an in vitro blood brain barrier model. FIG. 7B shows that POH decreased TEER, suggesting POH treatment increased paracellular permeability. TEER decreased when cells were treated by 0.03% POH for 20 hours compared to medium only, 0.01% POH treatment, and 0.02% POH treatment. The increase in TEER in each group over time corresponds to increased confluency of the cells in culture.

Figure 8:
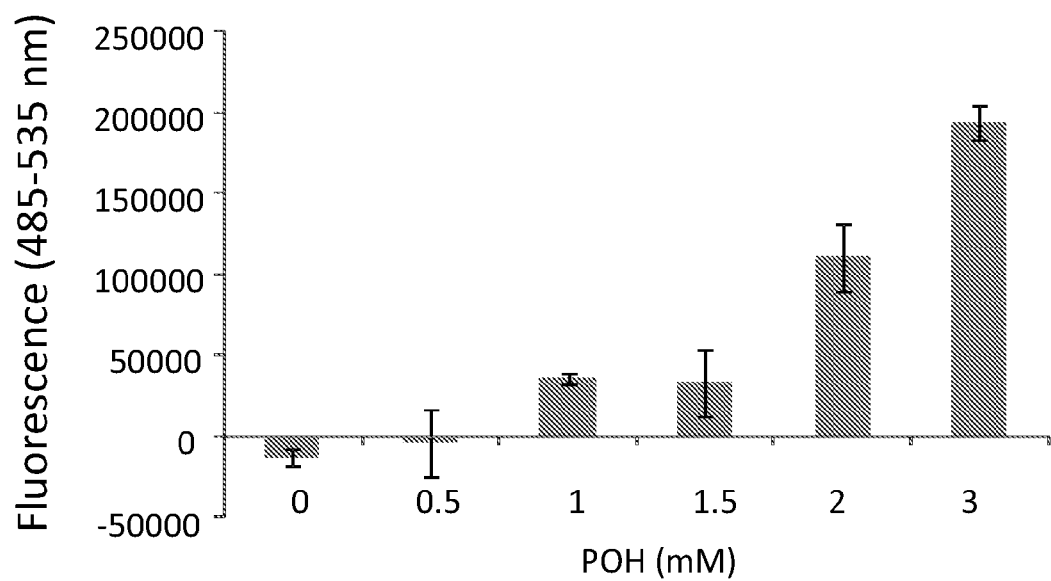
FIG. 8 shows that (S)-perillyl alcohol increases epithelial paracellular permeability. Madin-Darby Canine Kidney (MDCK) epithelial cells in a monolayer were treated overnight with varying concentrations of purified (S)-perillyl alcohol having a purity greater than 98.5%. Fluorescein labeled antibodies were then added to the cells. The amount of labeled antibodies that crossed the cell monolayer was then quantitated by fluorescence.

FIG. 8 shows that purified (S)-perillyl alcohol increases epithelial paracellular permeability. This result suggests that purified (S)-perillyl alcohol may increase BBB permeability. $2.5 \times 10^5$ Madin-Darby Canine Kidney (MDCK) cells were seeded in each well of the cell culture plate and cultured for 5 days. The cell culture media were changed 3 days after seeding and 24 hours before being treated with POH. MDCK cells in a monolayer were treated overnight with varying concentrations of purified (S)-perillyl alcohol having a purity greater than 98.5%. Fluorescein labeled antibodies were then added to the cells and incubated for 2 hours. The amount of labeled antibodies that crossed the cell monolayer was then quantitated by fluorescence.

Figure 10:
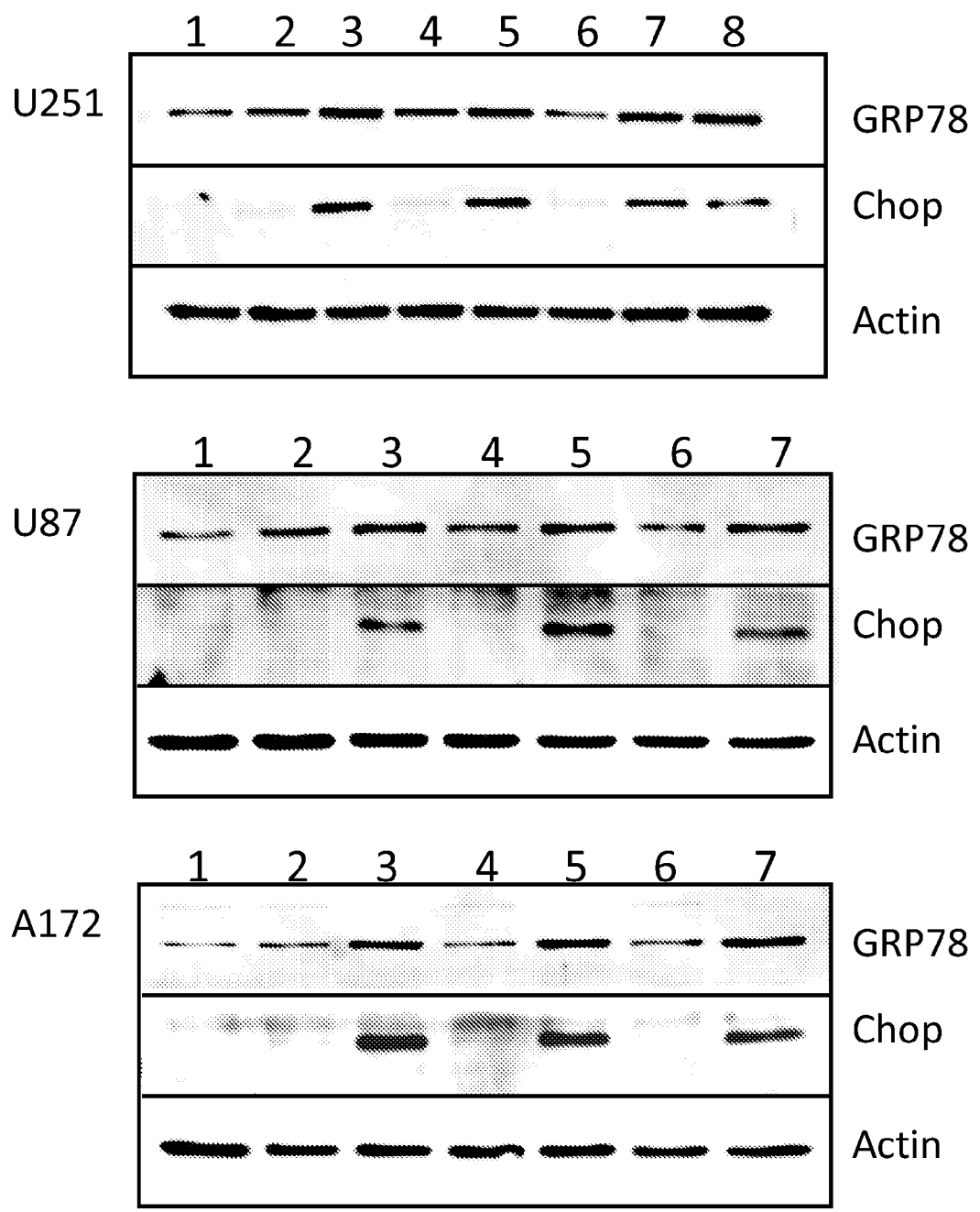
FIG. 10 shows Western blot results demonstrating that POH induces endoplasmic reticulum (ER) stress. POH upregulated the levels of ER stress marker glucose-regulated protein 78 (GRP78) and apoptosis markere CCAAT/enhancer binding protein (CHOP) in U251, U87 and A172 human glioma cells. The treatments for different lanes of the Western blot are as follows: 1: No treatment; 2: 0.5 mM purified POH; 3: 1.5 mM purified POH; 4: 0.5 mM Sigma POH; 5: 1.5 mM Sigma POH; 6: 0.5 mM Wako POH; 7: 1.5 mM Wako POH; 8: Positive Control (DMC 40 uM). Sigma POH is the POH purchased from Sigma Chemicals. Wako POH is the POH purchased from Sigma Chemicals. Cells were treated with different agents or mock treated for 20 hours before being lysed.

POH also induced endoplasmic reticulum (ER) stress via interaction with cytosolic proteins. POH up-regulated the levels of ER stress marker glucose-regulated protein 78 (GRP78) and apoptosis marker CCAAT/enhancer binding protein (CHOP) in various human glioma cell lines, including U251, U87 and A172 cells (FIG. 10). GRP78 is an anti-apoptotic protein the level of which is increased in response to stress. CHOP is a proapoptotic protein signaling for apoptosis. Pyrko et al. The unfolded protein response regulator GRP78/BiP as a novel target for increasing chemosensitivity in malignant gliomas. *Cancer Research* 67(20):9809-16, 2007.

Figure 11:
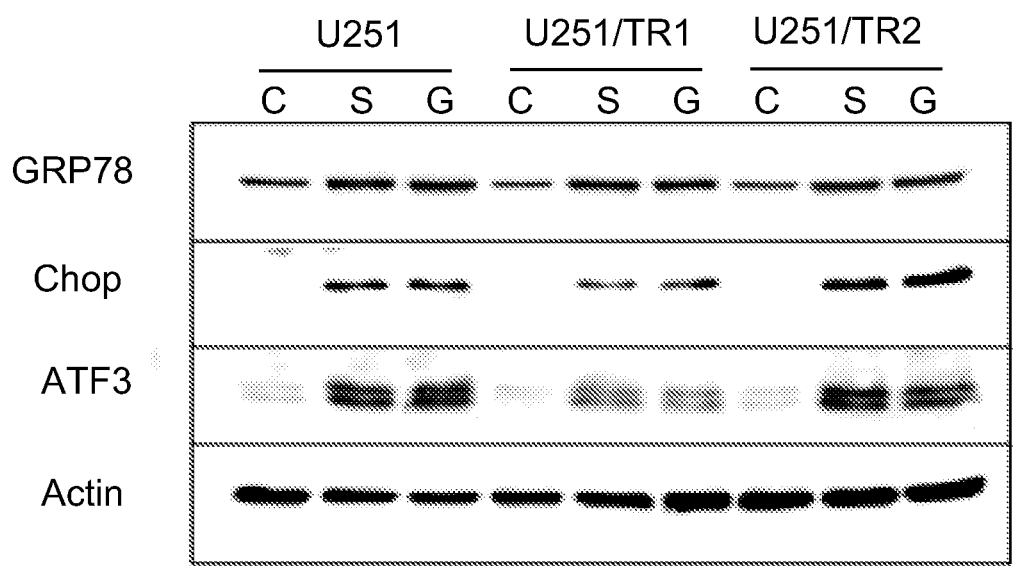
FIG. 11 shows Western blot performed after U251 TMZ-sensitive and TMZ-resistant (U251/TR1, U251/TR2) cells were treated for 20 hours with Sigma POH (1.5 mM; "S"), purified (S)-perillyl alcohol (1.5 mM; "G"), or not treated (control; "C"). The results demonstrate increased levels of glucose-regulatory protein 78 (GRP-78) and the apoptosis marker CHOP, showing increased endoplasmic reticulum (ER) stress after treatment. Sigma POH is the POH purchased from Sigma Chemicals.

U251 TMZ-sensitive and TMZ-resistant (U251/TR1, U251/TR2) cells were treated with Sigma POH (1.5 mM) or purified POH (1.5 mM) for 20 hours, then Western blot was performed. The results show that Sigma POH and purified POH increased expression of glucose-regulatory protein 78 (GRP-78) and the apoptosis marker CHOP, suggesting increased endoplasmic reticulum (ER) stress after treatment (FIG. 11).

EXAMPLE 10

POH Effectively Kills Cancer Stem Cells

Figure 13:
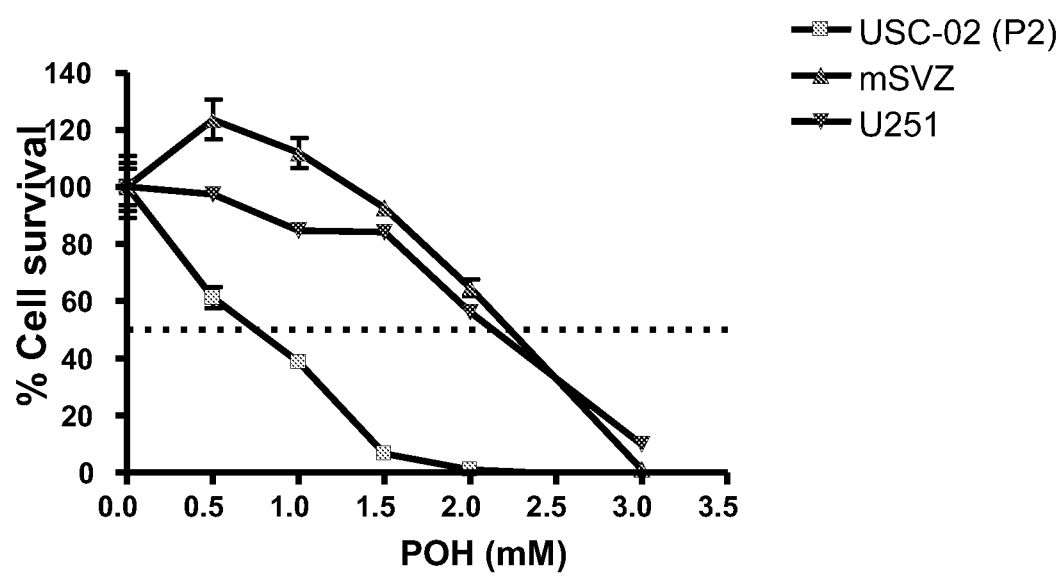
FIG. 13 shows the results of the MTT cytotoxicity assays demonstrating the efficacy of POH in killing USC-02 glioblastoma cancer stem cell line. The cancer stem cells were more sensitive to POH than glioma tumor cells (U251 cells) or normal stem cells (mSVZ: mouse SVZ stem/progenitor cells).
Figure 14:
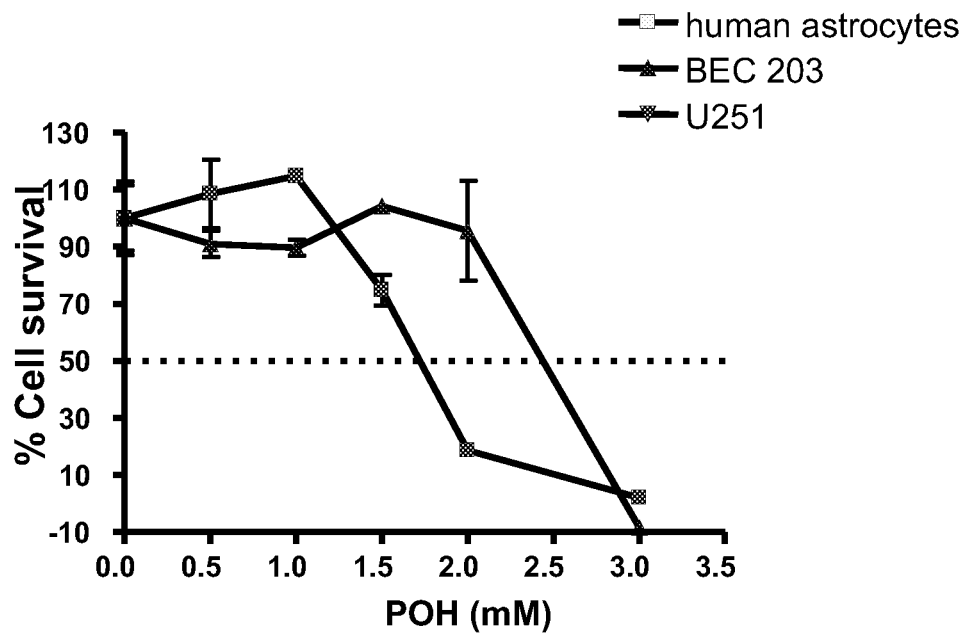
FIG. 14 shows the results of the MTT cytotoxicity assays demonstrating that the glioma tumor cells (U251 cells) were more sensitive to POH than normal brain cells (brain endothelial cells (BECs) and astrocytes).
Figure 14:
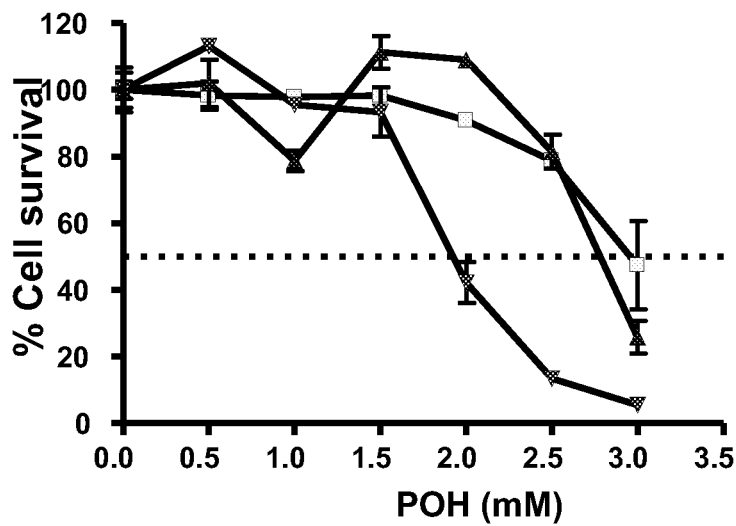
Figure 15A:
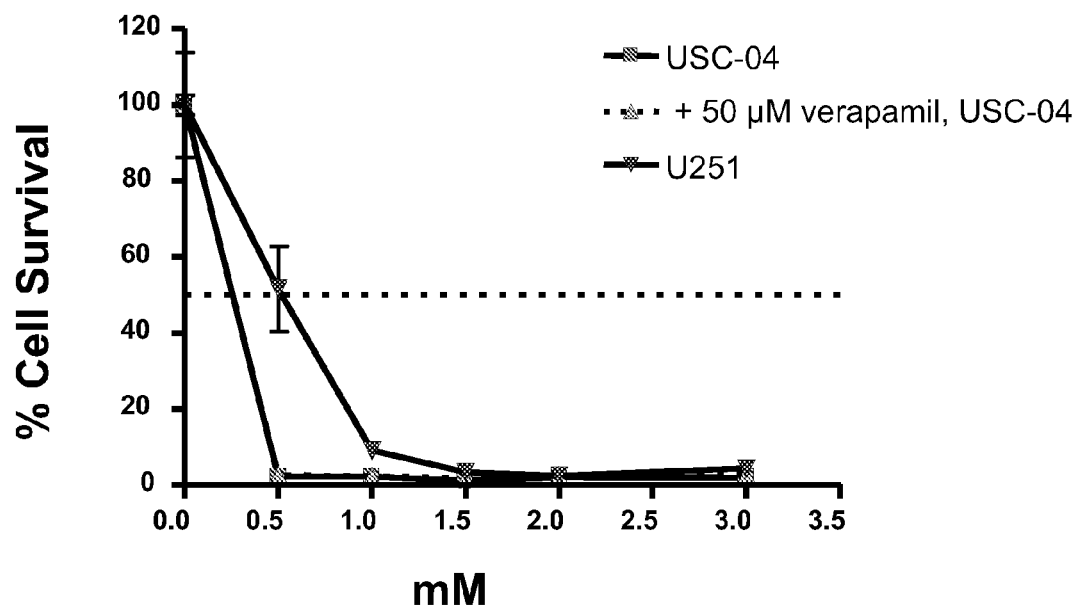
FIG. 15A shows the results of the MTT cytotoxicity assays demonstrating that the cancer stem cells USC-04 were more sensitive to POH than glioma tumor cells (U251 cells).
Figure 15B:
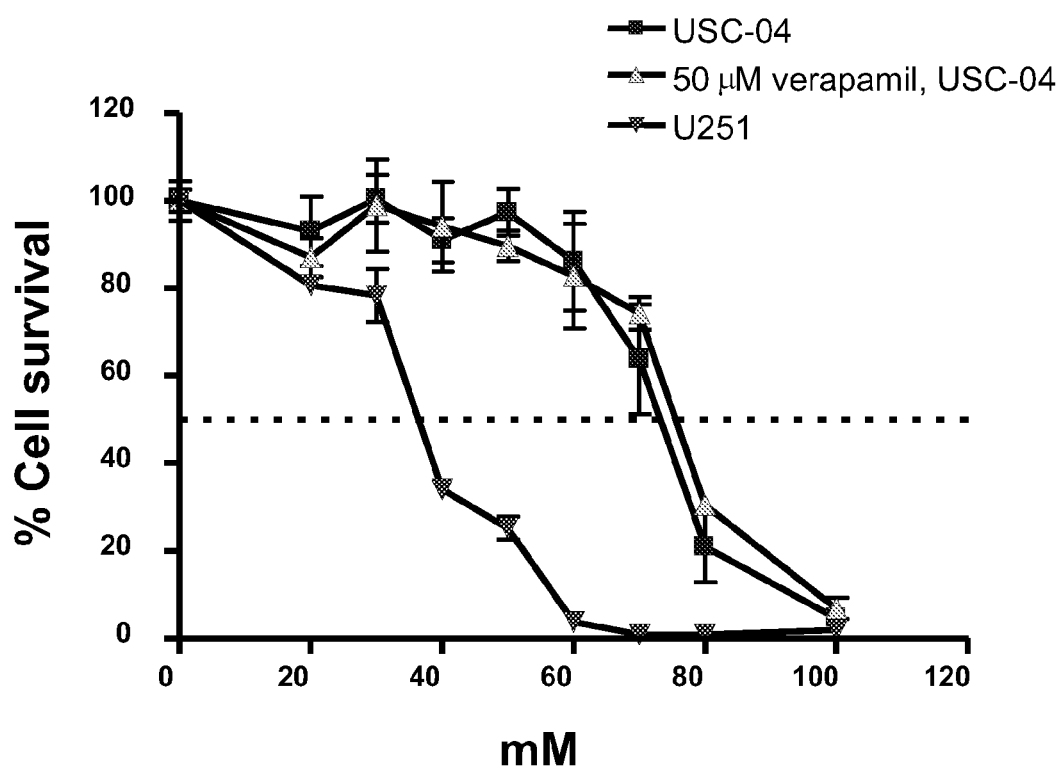
FIG. 15B shows the results of the MTT cytotoxicity assays demonstrating that the cancer stem cells USC-04 were more resistant to DMC than glioma tumor cells (U251 cells). Verapamil is used as an inhibitor of drug efflux pump proteins such as P-glycoprotein. The results suggest that DMC resistance of the cancer stem cells was not due to drug efflux via P-glycoprotein.

FIG. 13 shows the results of the MTT assay performed using glioblastoma cancer stem cell line USC-02, glioma tumour cells (U251 cells) or normal stem cells (mSVZ: mouse SVZ stem/progenitor cells) treated with POH for 48 hrs. The cancer stem cells were more sensitive to POH than glioma tumour cells (U251 cells) or normal stem cells (mSVZ: mouse SVZ stem/progenitor cells). FIG. 14 shows that the glioma tumor cells (U251 cells) were more sensitive to POH than normal stem cells (brain endothelial cells (BECs) and astrocytes). FIG. 15A shows the results of the MTT cytotoxicity assays demonstrating that the cancer stem cells USC-04 were more sensitive to POH ($EC_{50}$ on USC-04=0.3 mM) than glioma tumor cells (U251 cells). FIG. 15B shows the results of the MTT cytotoxicity assays demonstrating that the cancer stem cells USC-04 were more resistant to DMC ($EC_{50}$ on USC-04=78 µM) than glioma tumor cells (U251 cells). Verapamil is used as an inhibitor of drug efflux pump proteins such as P-glycoprotein. The results suggest that DMC resistance of the cancer stem cells was not due to drug efflux via P-glycoprotein.

Figure 16:
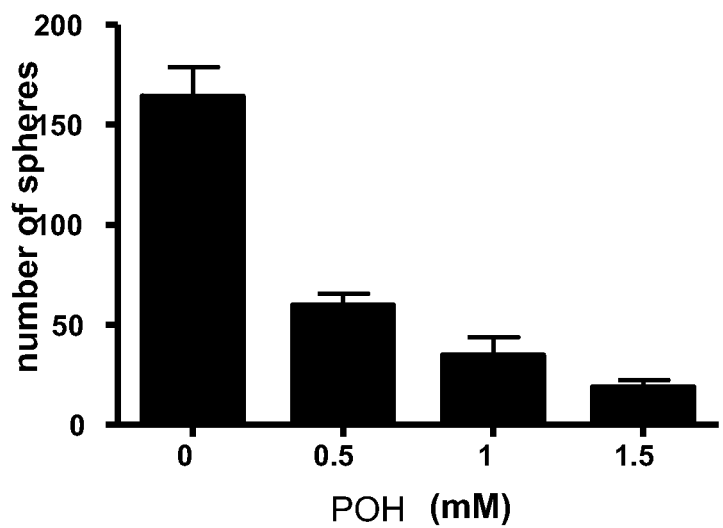
FIG. 16 shows the results of sphere formation assay (SFA) demonstrating that POH decreased the number of spheres formed in glioblastoma cancer stem cells (USC04). USC04 cells were incubated with varying concentrations of POH (0-1.5 mM) for 6 days.

FIG. 16 shows the results of sphere formation assay (SFA) demonstrating that POH decreased the number of spheres formed in glioblastoma cancer stem cells (USC04). USC04 cells were incubated with varying concentrations of POH (0-1.5 mM) for 6 days.

Figure 17:
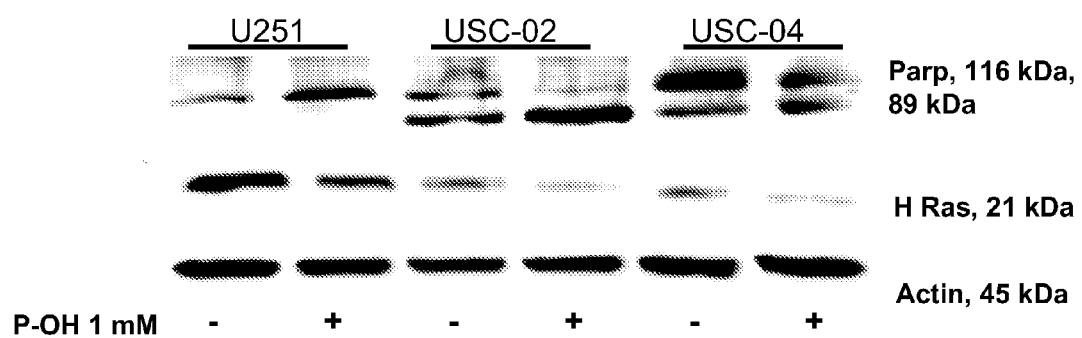
FIG. 17 shows that POH decreased H-ras production in glioblastoma cancer stem cells. Two glioblastoma cancer stem cell lines (USC-02, USC-04) were treated by POH for 24 hours. USC-02 and USC-04 are two independent primary cancer stem cell lines isolated from glioblastoma tissue from two different patients.
Figure 18:
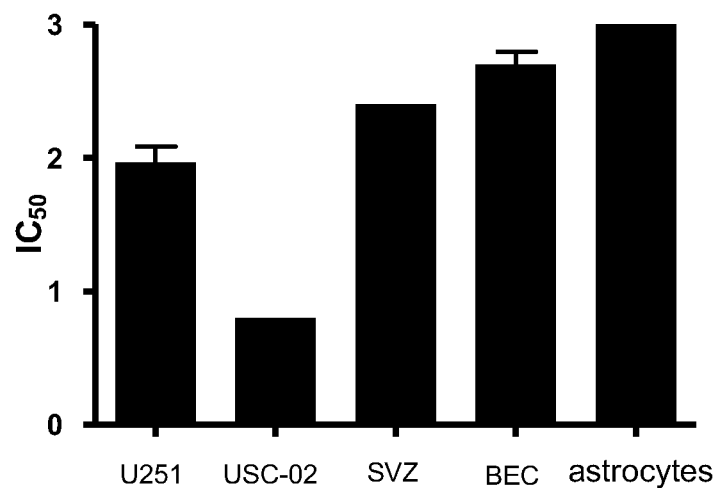
FIG. 18 shows comparison of POH IC50 values on various cell lines. Cancer stem cells (USC-02 cells) are the most sensitive to POH among the cell lines tested. Normal cells, including normal stem cells mSVZ (mouse SVZ stem cells), brain endothelial cells (BECs) and astrocytes, are the most resistant to POH.

FIG. 17 shows that POH decreased H-ras production in glioblastoma cancer stem cells. Two glioblastoma cancer stem cell lines (USC-02, USC-04) were treated by POH for 24 hours. USC-02 and USC-04 are two independent primary cancer stem cell lines isolated from glioblastoma tissue from two different patients.

EXAMPLE 11

In Vivo Animal Studies

The purified POH prepared by the process in Example 1 will be placed into an intranasal inhaler (e.g., the ViaNase Electronic Atomizer from Kurve Technology (Bethell, Washington)). The intranasal delivery system from Kurve Technology is capable of accurately delivering a pre-determined drug volume (e.g., from 0.2-6 mL). The device is loaded and cleaned in the same manner as a pulmonary nebulizer. The device can deliver the drug to the olfactory region in bench testing, in animals and humans.

Male athymic nu/nu mice (6-8 weeks old) will be employed for this research. Rodent subcutaneous/intracranial glioma model can be established as follows. Six to eight week old athymic nu/nu mice will be anesthesized with intraperitoneal injections of ketamine (80 mg/kg) and xylazine (10 mg/kg). For the intracranial glioma model, the mice are placed into a stereotactic head frame (Harvard Apparatus), and local anesthetic (0.2 cc of 0.25% xylocaine) is injected into the right frontal scalp. A knife blade is used to make a small incision, and a drill bit is used to make a small opening in the right frontal skull at the level of the coronal suture. Glioma cells ($1 \times 10^5$ cells/10 µl), for example, U-87 human glioma cells, will be loaded into a calibrated Hamilton syringe. The needle tip will be placed precisely into the right frontal lobe of the rat, and cells will be slowly injected using a control push from the Hamilton syringe. After the injection is finished, the syringe and needle will be removed, and the wound closed.

Two weeks after surgical implantation, the mice will be divided into 4 groups (6 mice/group) and will be treated, respectively, with: saline drops alone (control), crude POH from Sigma (0.03%, 50 ul/drop, one drop per nostril), POH (purified to greater than 98.5% purity; 0.03%, 50 ul/drop, one drop per nostril), and TMZ (5 mg/kg, oral gavage). TMZ serves as the positive control.

Brains will be harvested, and tumor size determined. Survival curves will be constructed by following the mice until they develop neurological deficits. Our experience has been that survival is about four weeks after implantation for untreated mice, and up to 8 weeks for mice treated with TMZ.

We will also use an immune-competent syngeneic rat model where RG2 rat glioma cells ($1 \times 10^5$ cells/10 ul) will be implanted into the right frontal lobe of Fisher 344 rats. Rats will be divided into the same 4 groups as above. We will also examine the anti-invasion properties of POH using the rat RG2 model, because the RG2 cells can freely migrate, and thus, invade in the rat parenchyma.

EXAMPLE 12

Patient Studies

In a recent clinical research in Brazil, intranasal delivery of perillyl alcohol in patients with recurrent malignant gliomas resulted in regression or stabilization of the disease, with 50% of the 140 treated patients achieving 6 month progression-free period and several patients enjoying as many as 3 years of disease remission. Furthermore, side effects from the treatment were almost non-existent. Da Fonseca et al. Correlation of tumor topography and peritumoral edema of recurrent malignant gliomas with therapeutic response to intranasal administration of perillyl alcohol. *Invest New Drugs* 2009, January 13.

We will deliver the purified POH (having greater than 98.5% purity) intranasally to patients suffering from malignant gliomas. To investigate whether POH can be delivered directly to the brain tumor cells, the distribution of the purified POH will be studied by delivering $^{11}C$ labeled-POH to the patients, followed by positron emission tomography (PET) imaging. The patients will then undergo a limited therapeutic trial using escalating doses of inhalational POH. The patients will be dose escalated using groups of three, with each group receiving intranasal purified POH (with purity greater than 98.5%) at 0.05% (w/v), 1% (w/v), 1.5% (w/v), 2% (w/v), 2.5% (w/v). The 2% (w/v) is what is currently used in Brazil. Delivery will be via the ViaNase nasal inhaler and will be given three times per day. PET Imaging Studies. Ten patients with pathologically confirmed malignant glioma will be scanned following intranasal inhalation of 5-10 mCi of the $^{11}C$-POH formulation using a Siemens Biograph TruePoint HD PET/CT scanner. Static imaging will begin at 30 minutes following inhalation using 10-minute acquisition in a single bed position overlying the cranium. Subsequent serial acquisitions will occur at 30-minute intervals for 2 hours to assess progressive accumulation in brain and tumor tissue. Depending on patient compliance and levels of remaining and accumulated activity, we will attempt to image beyond 2 hours. Co-registered PET/CT images will be compared with contrast enhanced MRI studies on all patients to assess correlation of activity accumulation with enhancement patterns.

The scope of the present invention is not limited by what has been specifically shown and described hereinabove. Those skilled in the art will recognize that there are suitable alternatives to the depicted examples of materials, configurations, constructions and dimensions. Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety. Variations, modifications and other implementations of what is described herein will occur to those of ordinary skill in the art without departing from the spirit and scope of the invention. While certain embodiments of the present invention have been shown and described, it will be obvious to those skilled in the art that changes and modifications may be made without departing from the spirit and scope of the invention. The matter set forth in the foregoing description and accompanying drawings is offered by way of illustration only and not as a limitation.

What is claimed is:

1. A process for purifying (S)-perillyl alcohol comprising the steps of:
   (a) derivatizing a mixture comprising (S)-perillyl alcohol to form a perillyl alcohol derivative;
   (b) crystallizing the perillyl alcohol derivative;
   (c) separating the perillyl alcohol derivative;
   (d) releasing the (S)-perillyl alcohol from the separated perillyl alcohol derivative from step (c) by hydrolysis; and,
   (e) isolating the (S)-perillyl alcohol from step (d),
wherein the isolated (S)-perillyl alcohol has a purity of greater than about 98.5% (w/w).

2. The process of claim 1, wherein the perillyl alcohol derivative is a perillyl alcohol ester.

3. The process of claim 2, wherein the ester is benzoate ester.

4. The process of claim 3, wherein the benzoate ester I 3,5-dinitrobenzoate ester.

5. The process of claim 1, wherein the isolated (S)-perillyl alcohol has a purity of greater than about 99.0% (w/w).

6. The process of claim 5, wherein the isolated (S)-perillyl alcohol has a purity of greater than about 99.5% (w/w).

7. The process of claim 1, wherein the mixture further comprises natural-product-derived or other impurities.

8. The process according to claim 1, wherein the hydrolysis is accomplished in the presence of NaOH, an alcoholic solvent and water.

9. The process according to claim 8 wherein the alcoholic solvent is methanol.

* * * * *

UNITED STATES PATENT AND TRADEMARK OFFICE
CERTIFICATE OF CORRECTION

| | | |
|---|---|---|
| PATENT NO. | : 9,498,448 B2 | Page 1 of 1 |
| APPLICATION NO. | : 14/843097 | |
| DATED | : November 22, 2016 | |
| INVENTOR(S) | : Thomas Chen et al. | |

It is certified that error appears in the above-identified patent and that said Letters Patent is hereby corrected as shown below:

In the Specification

After the "CROSS REFERENCE TO RELATED APPLICATIONS" Column 1, Line 15, insert as follows:
-- STATEMENT OF GOVERNMENT SUPPORT
This invention was made with government support under CA217551 awarded by the National Institutes of Health. The government has certain rights in the invention. --

Signed and Sealed this
Twenty-seventh Day of May, 2025

Coke Morgan Stewart
*Acting Director of the United States Patent and Trademark Office*